(12) United States Patent
Valentini et al.

(10) Patent No.: US 7,001,332 B1
(45) Date of Patent: Feb. 21, 2006

(54) SURGICAL DEFLECTOR TOOL

(75) Inventors: Valerio Valentini, Montreal (CA);
Anthony Paolitto, St. Leonard (CA);
Raymond Cartier, Montreal (CA)

(73) Assignee: Coroneo Inc., Montreal (CA)

( * ) Notice: Subject to any disclaimer, the term of this patent is extended or adjusted under 35 U.S.C. 154(b) by 283 days.

(21) Appl. No.: 10/111,899

(22) PCT Filed: Nov. 8, 2000

(86) PCT No.: PCT/CA00/01336

§ 371 (c)(1),
(2), (4) Date: Apr. 30, 2002

(87) PCT Pub. No.: WO01/34034

PCT Pub. Date: May 17, 2001

(30) Foreign Application Priority Data

Nov. 8, 1999 (CA) .................................. 2289871

(51) Int. Cl.
*A61B 1/32* (2006.01)
(52) U.S. Cl. ...................................... 600/210
(58) Field of Classification Search ............. 600/206, 600/210, 216, 227, 228, 229; 606/232, 233
See application file for complete search history.

(56) References Cited

U.S. PATENT DOCUMENTS

| 4,617,916 | A  | * | 10/1986 | LeVahn et al. | 600/228 |
| 6,120,436 | A  | * | 9/2000  | Anderson et al. | 600/201 |
| 6,626,830 | B1 | * | 9/2003  | Califiore et al. | 600/229 |
| 2001/0044572 | A1 | * | 11/2001 | Benetti et al. | 600/235 |
| 2002/0004628 | A1 | * | 1/2002  | Alexander et al. | 585/660 |
| 2002/0111537 | A1 | * | 8/2002  | Taylor et al. | 600/210 |
| 2003/0060686 | A1 | * | 3/2003  | Taylor et al. | 600/210 |
| 2003/0187333 | A1 | * | 10/2003 | Spence et al. | 600/210 |

* cited by examiner

*Primary Examiner*—Eduardo C. Robert

(57) ABSTRACT

A suture deflector for retracting a body tissue by deflecting a surgical suture that is simultaneously attached to a body tissue and a surgical retractor. The suture deflector imparts a deflecting force on the surgical suture to retract a body tissue between a first and second retracted position. The suture deflector consists of a securing mechanism for attaching the suture deflector to a surgical retractor and a deflection member extending from the securing mechanism. The deflection member includes a suture contacting section that is configured so as to prevent the severing of the surgical suture when it is deflected by the suture deflector. In certain embodiments, the deflection member includes a connecting section that extends between the securing mechanism and the suture contacting section and that is also movable relative to the securing mechanism in order to impart a deflecting force on the surgical suture.

24 Claims, 25 Drawing Sheets

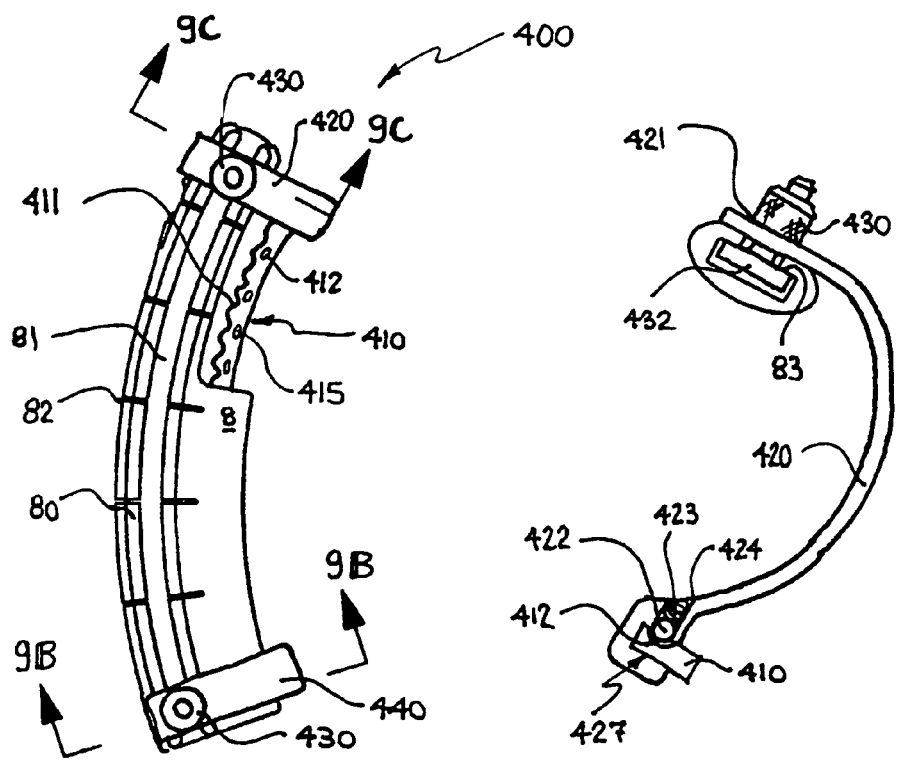
FIGURE 9A
FIGURE 9C
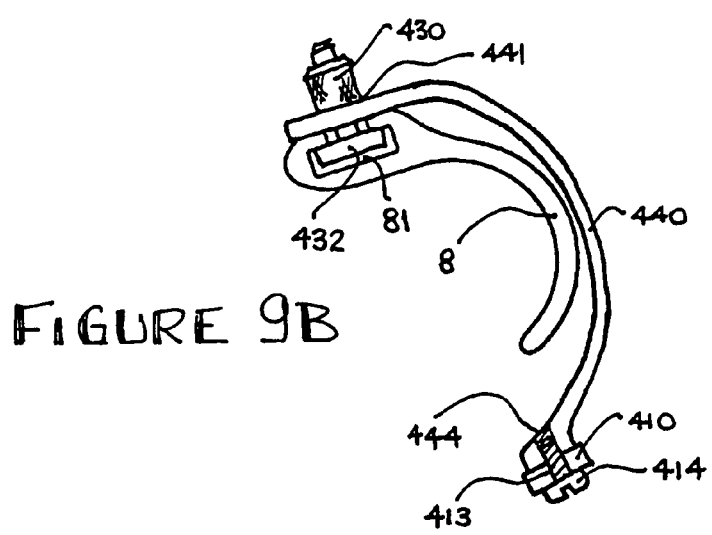
FIGURE 9B

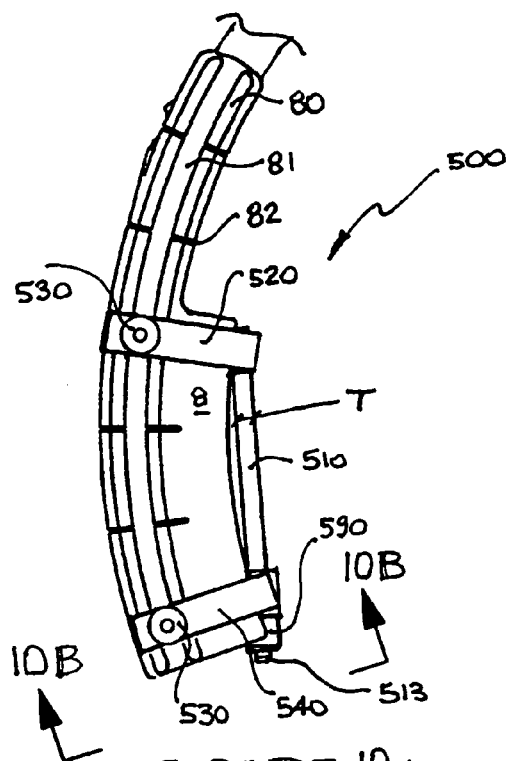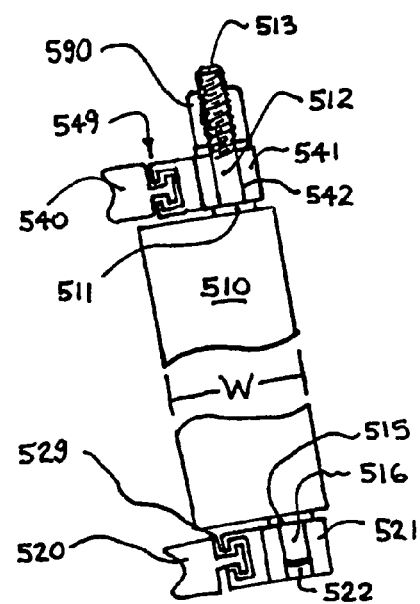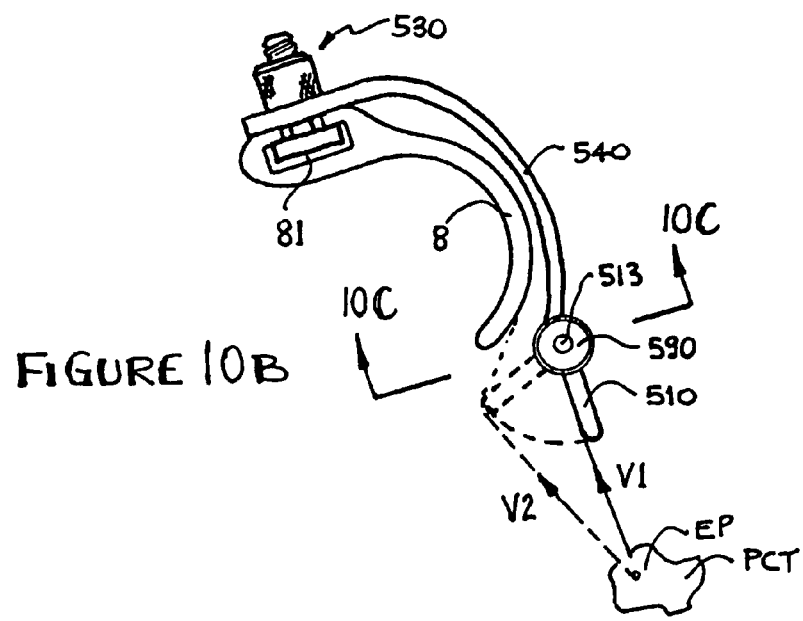
FIGURE 10A
FIGURE 10C
FIGURE 10B

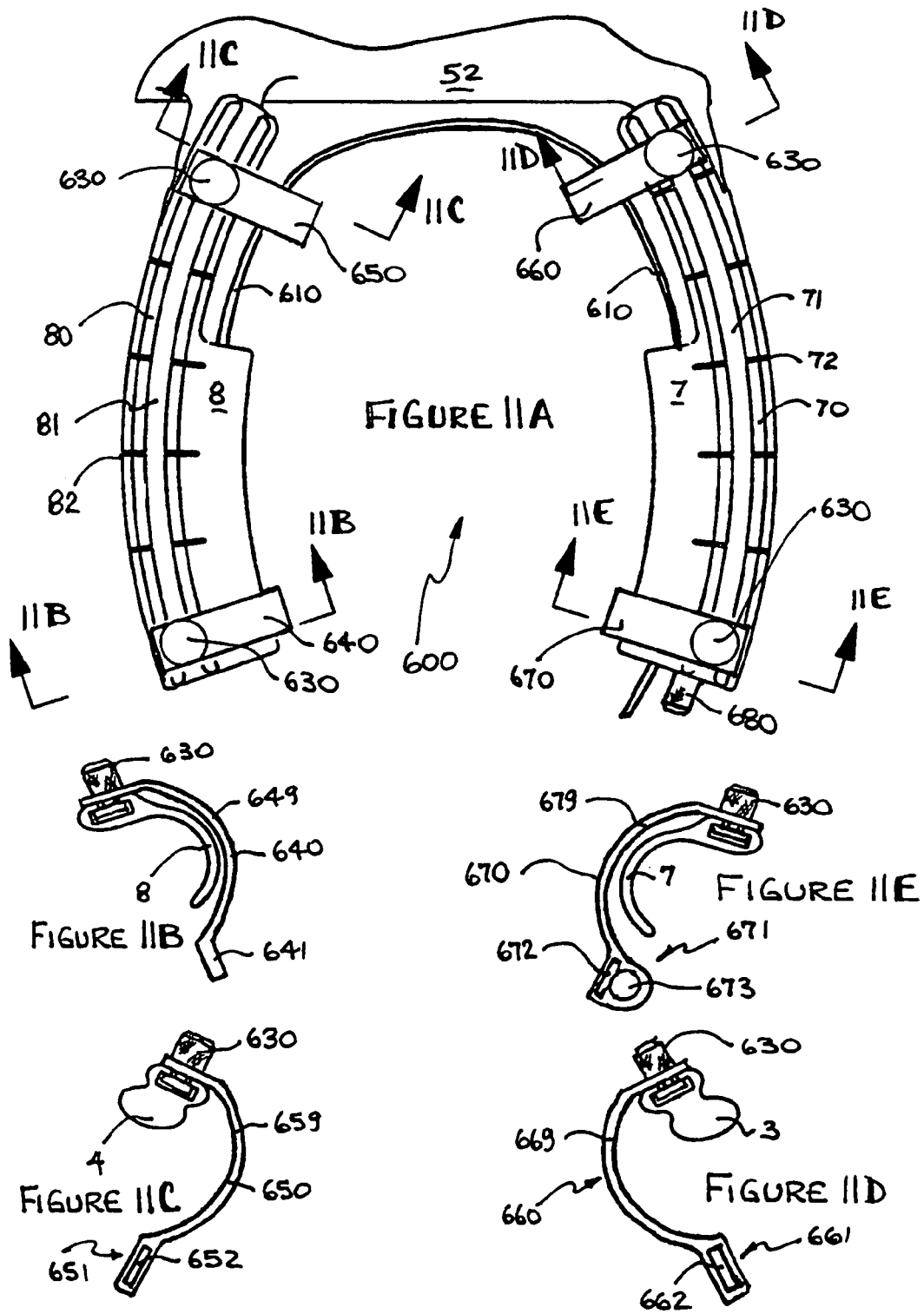

SURGICAL DEFLECTOR TOOL

FIELD OF THE INVENTION

The present invention relates to the field of surgical apparatus and more specifically, to a surgical apparatus for deflecting a tissue retraction means.

BACKGROUND OF THE INVENTION

Cardiac surgery generally requires an incision through the patient's skin, underlying muscle and tissue, and often a retraction of the patient's ribcage in order to access the patient's underlying coronary organs. Traditional cardiac surgery has been commonly performed through a midline sternotomy incision, where the patient's sternum is incised and the ribcage retracted to obtain access to the patient's heart and major blood vessels. More recently, in minimally invasive procedures, smaller parasternal incisions (mini-sternotomy) or intercostal thoracotomy approaches have also been employed. In thoracotomy approaches, two adjacent ribs are spread apart at times even removing a length of rib to improve access into the patient's thorax and to the patient's heart. In these approaches, a chest retractor is used to spread apart the patient's skin and thoracic bone structure to maintain an incised opening, or surgical window, onto the underlying cardiac tissue.

Chest retractors exist in many sizes and shapes and have been present since the dawn of cardiac surgery. Most known chest retractors have an elongate rack bar and two retracting arms, namely a fixed retracting arm and a movable retracting arm. Both arms typically extend in a direction normal to the rack bar. The movable arm can be displaced along the rack bar, and relative to the fixed arm, by using a crank to activate a pinion mechanism which engages teeth on the rack bar. Two blades are generally provided, usually disposed below the retractor arm and extending into the surgical incision, to interface with the patient's skin or thoracic bone structure. These two blades apply the retraction that creates the surgical window by the relative movement, and an ensuing spacing apart, of the two retractor arms. In addition, chest retractors may also serve as a substantially stable surgical platform for engaging surgical apparatus used during the course of the surgical intervention. Through this engagement with the chest retractor, the surgical apparatus may be set in a substantially stable position or orientation relative to cardiac tissue implicated in the surgical intervention. Cardiac tissue includes pericardium, epicardium, myocardium, endocardium, tissue of the septal wall, aorta tissue, vena cava tissue, cardiac valves, heart muscle, the coronary arteries and veins, the pleurae, the thymus, and other like anatomical tissue.

One type of cardiac surgery known as coronary artery bypass graft (CABG) surgery has been traditionally performed with the support of a cardio-pulmonary machine, whereby the patient's blood is oxygenated outside the body through extracorporeal circulation (ECC). This allows the surgeon to perform surgical procedures on a perfectly still heart while the patient's life support is maintained by cardio-pulmonary assistance. During traditional CABG surgery, the surgeon or assistant may manually or otherwise manipulate the arrested heart into a position and orientation that yields the best access to a target artery requiring a bypass graft. The great majority of CABG surgeries (approximately 70%) are triple vessel bypass surgeries; that is, at least one bypass graft is performed on each of the anterior, inferior and posterior artery beds of the patient's heart.

Recently, in an aim to render CABG surgery less invasive to the patient, beating heart CABG surgery is being developed whereby ECC, one of the most invasive aspects of cardiac surgery, is eliminated and coronary artery revascularization is performed directly on the beating heart. One of the challenges in performing beating heart CABG surgery lies in positioning and orienting the beating heart in order to obtain access to the inferior and posterior artery beds, while aiming to minimize physiologically undesirable effects such as hemodynamic instability, arrhythmia, or a precipitous drop in arterial pressure, any of which may occur as a result of such beating heart manipulations. Furthermore, a surgical device placed directly in contact with the beating heart which enables manipulations of the beating heart or which restrains its movement or positioning may impose loads and constraints on the beating heart. This may impede the normal beating function of the heart and induce the onset of the physiologically undesirable effects described above. In traditional CABG surgery, the heart is arrested and therefore heart manipulations are well tolerated.

During CABG surgery or beating heart CABG surgery, the pericardium, namely a substantially thin membranous tissue forming a sac in which the heart and the commencement of the major blood vessels connecting with the heart are contained, is generally incised and unraveled to expose at least a portion of the heart surface which is to receive the bypass graft. The pericardium tissue, unlike the heart, is not beating and it may be separated from the heart surface except in certain locations where it is anatomically attached to the heart. Thus, it is surgically possible in CABG surgery, to position and orient the heart through retraction of the pericardium tissue to obtain access to the inferior and posterior coronary artery beds. In beating heart CABG, heart manipulations achieved through retraction of the pericardium tissue tend to reduce the likelihood of inducing trauma to the beating heart, tend to not distort the heart's chambers that may compromise blood ejection capacity, and tend to minimize the physiologically undesirable effects mentioned above, since direct contact with the beating heart is avoided. One such beating heart manipulation consists of "verticalizing" the heart in order to gain access to the posterior artery bed. In this maneuver, the pericardium is engaged close to the base of the heart with one or more tissue retraction means (preferably 1 to 1.5 inches away from the pericardial reflection) and the apex of the heart is rotated outward from the retracted chest cavity through the tensile loads applied to the engaged pericardium. The longitudinal axis of the beating heart thereby assumes substantially vertical orientation (with the patient lying in a supine position on the operating table).

Pericardial retraction may be achieved through a variety of tissue retraction means. Sutures such as traction or stay sutures have been generally employed in cardiac surgery and are one such means of achieving pericardial traction. Sutures generally consist of a tissue piercing member such as a relatively sharp needle and a length of wire-like filament such as a suture line integrally attached to the blunt end of said needle. In the application of pericardial traction sutures, the needle pierces the pericardium tissue, a certain length of suture line is then threaded through the pierced pericardium tissue, and the resultant two ends of the suture line (i.e. the length between the pierced tissue and the free end of the suture line and the length between the pierced tissue and the needle-bearing end of the suture line) are then simultaneously pulled to impart the retraction load on the pericardium tissue and consequently displace the beating heart which is anatomically attached to said pericardium tissue.

In order to "verticalize" a beating with pericardial traction sutures, a number of such sutures must be inserted through and engaged with the pericardium tissue preferably along its pericardial reflection in order to get the desired lifting of the apex and consequently a good exposure to the posterior coronary bed. For example, one traction suture may be placed between the superior and inferior pulmonary vein, a second one below the inferior pulmonary vein, a third one midway between the apex of the heart and the inferior pulmonary vein, and a fourth one towards the diaphragmatic face near the inferior vena cava. Pericardium retraction loads are subsequently applied to each of these traction sutures independently. The resultant lengths of suture line must then be secured to a stable surgical platform such as a chest retractor to maintain the desired retraction load on the pericardium tissue. Standard surgical clamps may be used to secure the two resultant lengths of suture line relative to the chest retractor through a variety of methods. Alternatively, a tissue retraction means consisting of a suture line with an associated anchoring means may also be used to apply and maintain the pericardial traction loads, and also the resultant heart position and orientation relative to the chest retractor. Such types of tissue retraction means are described more fully in co-pending Canadian patent application Serial No. 2,242,295 filed on Aug. 10, 1998 in the names of Paolitto et al. and entitled "Surgical Instruments for Tissue Retraction", for which a corresponding PCT application Serial No. PCT/CA99/00740 has been filed on Aug. 10, 1999 in the names of Paolitto et al. and entitled "Surgical Suture and Associated Anchoring Mechanism for Tissue Retraction". In both these methods of applying pericardial retraction, the engagement of the pericardium tissue is achieved through piercing of said pericardium tissue.

Alternatively, another type of tissue retraction means may consist of engaging the pericardium tissue with a negative pressure suction force. The suction force may be applied through a flexible suction port. A retraction load may be imposed by pulling on the flexible tubular conduits which communicate the negative pressure to the said suction port from a negative pressure source. The said retraction load is maintained by securing a part of this negative pressure apparatus, most commonly the flexible tubular conduit, relative to a stable surgical platform such as a chest retractor. Such types of negative pressure tissue retraction means are described more fully in co-pending Canadian patent application Serial No. 2,242,766 filed on Aug. 17, 1998 in the names of Paolitto et al. and entitled "Pericardium Retraction Device for Positioning a Beating Heart", for which a corresponding PCT application Serial No. PCT/CA99/00757 has been filed on Aug. 17, 1999 in the names of Paolitto et al. and entitled "Pericardium Retraction Device for Positioning a Beating Heart." In yet other types of tissue retraction means, the pericardium tissue may be engaged by tissue-grasping or tissue-clamping members which grasp or clamp at least a portion of said pericardium tissue.

To maintain the position and orientation of the beating heart achieved through pericardial traction, the tissue retraction means is secured at its anchoring location to a suitable substantially stable surgical platform such as a chest retractor. As will be illustrated and described more fully below, once the pericardial retraction load is secured, a vector may be defined originating from the point of engagement of the tissue retraction means with the pericardium tissue and generally directed along the tissue retraction means towards a point of anchoring on a suitable surgical platform.

Often times within a retracted chest cavity, the projected distance between a deployed tissue retraction means and the heart surface may be small and restrictive for certain types of surgical interventions. This is more often the case when the patient's ribcage is retracted a minimum amount, when the patient's heart is enlarged due to disease, or when the pericardium tissue is engaged with a tissue retraction means in a deep location close to the pericardial reflection. For instance, in a beating heart revascularization of a posterior coronary artery, with the patient's heart verticalized through pericardial retraction, the projected distance between the pericardial traction sutures and the posterior heart surface may be small or restrictive that it may hinder not only the deployment of coronary stabilizers that immobilize the portion of beating heart around the posterior target artery, but may also compromise the quality of the posterior artery bypass graft.

In another type of cardiac surgery such as mitral valve surgery, surgical access to the diseased mitral valve is mostly achieved through a surgical incision of the left atrium. To attempt to achieve optimal exposure, the heart is elevated out of the chest and rotated, allowing the apex to drop posteriorly while elevating the right side of the heart. This maneuver tends to bring the posterior mitral valve leaflet toward the right side of the patient in a plane which tends to face the surgeon, often permitting better visualization of the mitral valve and subvalvular structures. Following the median sternotomy, the pericardium is opened slightly to the right of the midline and the right side of the pericardium is sutured under tension to the chest wall or secured under tension to a point on a stable surgical platform in the nature of a chest retractor. This helps to provide the elevation of the right side of the heart. The pericardial edges on the left side of the incision are usually not suspended. After bicaval cannulation, the superior vena cava is usually mobilized by incising the pericardium above it. A tourniquet is often placed on the inferior vena cava and traction is applied in a general direction toward the patient's feet. This tourniquet may also be secured to the chest retractor. This procedure further helps to elevate the right side of the patient's heart. The left atrium is incised parallel to the intra-atrial groove. This incision is usually extended below the superior vena cava and a considerable distance below the inferior vena cava.

At times during cardiac surgery, the patient's heart surface or cardiac tissue is constrained by, or in close vicinity to, the patient's pleura and lungs. Access to the surgical intervention site on the patient's heart surface may have to be obtained by assistant-hand-held retractors deployed to displace the pleura and lungs.

It is therefore an object of the invention to provide a surgical deflector tool attempting to alleviate or eliminate the above-mentioned drawbacks.

It is a further object of the invention to provide a surgical deflector tool which tends to improve surgical access and visibility to a given body organ or body tissue where a surgical intervention is intended to take place, such as a coronary organ, cardiac tissue and the like.

BRIEF SUMMARY OF THE INVENTION

The invention provides a surgical deflector tool comprising a deflection member adapted for connection to a surgical platform, said deflection member, in use, being adapted to deflect at least a portion of a tissue retraction means when said tissue retraction means is simultaneously engaged with a body tissue and with said surgical platform.

For instance, the tissue retraction means may be deflected from an initial, non-deflected position prior to its engagement with said deflection member, to a second deflected position after engagement with said deflection member. When said body tissue is anatomically attached to a body organ, the deflection of the tissue retraction means relative to its initial position with respect to said organ, and prior to its engagement with said deflection member, is advantageously in a direction substantially away from the surface of said body organ.

During a cardiac surgery, such a surgical deflector tool advantageously provides a deflection member that is adapted to displace at least a portion of a deployed tissue retraction means engaged with the pericardium tissue anatomically attached to the heart, away from the portion of the heart surface that is situated in the general vicinity of where a surgical intervention is intended to take place. Consequently, the surgical access and surgeon's vision tends to be improved at the site of the intended surgical intervention.

During cardiac surgery, the pericardium tissue is generally incised along the anterior surface of the heart and generally along the heart's major axis. In certain instances, the tissue retraction means engages the pericardium tissue at a location close to the pericardial incision (and in the vicinity of the anchoring point of tissue retraction means to the chest retractor). As such, a deployed surgical deflector tool may be in contact with and deflect a portion of the pericardium tissue that is engaged with said tissue retraction means.

As described above, heart verticalization may be achieved through beating heart manipulations that are substantially well tolerated by the patient. In certain instances, such manipulations performed in conjunction with the deployment of a surgical deflector tool, tends to improve the likelihood of achieving complete coronary artery revascularization on the beating heart. Complete revascularization is considered by most to be the gold standard in revascularization surgery, which till date has been mostly achieved through traditional CABG.

In another example of cardiac surgery affecting the mitral valve, the surgical deflector tool may be used to displace or deflect at least a portion of a pericardium retraction suture used to position or orient the patient's heart within the retracted chest cavity. At times, the surgical deflector tool may be in contact with and displace or deflect a portion of the retracted pericardium tissue which, at some location is engaged with at least one pericardium retraction suture. Said deflections or displacements are in a direction away from the heart's surface tissue thereby tending to improve surgical access to the diseased mitral valve.

In another example of cardiac surgery, the surgical deflector tool of the invention is advantageously adapted to displace at least a portion of the pleura and lungs, or other like anatomic tissue, in a direction generally away from the patient's heart surface where a surgical intervention is intended to take place. At times, the pleura may be engaged with a tissue retraction means which is simultaneously secured to a chest retractor. As such, the surgical deflector tool may also be deployed to displace a lung through the deflection of a tissue retraction means that is in turn engaged with said pleura tissue. Alternatively, the surgical deflector tool may also be deployed to displace a lung through the contact with and deflection of the said pleura which is engaged at some location with a tissue retraction means, and said tissue retracting means is simultaneously anchored to a chest retractor. Similar advantages with other types of surgery, either cardiac or non-cardiac, may also be provided with the surgical deflector tool of the present invention.

In cardiac surgeries where the heart has been positioned or oriented through retraction of the pericardium tissue anatomically attached to said heart, the surgical deflector tool tends to improve surgical access to a target portion of the said heart where a surgical intervention is intended to take place, by deflecting at least a portion of the pericardium tissue which is engaged at some location with a tissue retraction means, or at least a portion of the tissue retraction means engaged with pericardium tissue, away from said target portion of said heart. As such, in CABG surgeries, the surgical deflector tool tends to improve the efficacy and quality of bypass grafts performed on an inferior or posterior coronary artery of a patient's heart by tending to enhance the surgeon's visibility and surgical access to the target artery. The deflector advantageously maintains at least a portion of the pericardium tissue which is engaged at some location with a tissue retraction means, or at least a portion of a tissue retraction means engaged with the pericardium tissue, away from the target portion of the patient's heart where the surgical intervention will take place.

In the various examples, the tissue retraction means may be a surgical suture, a negative pressure suction line, a grasping member, a clamping member, or other like tissue retraction member. The surgical platform is preferably a chest retractor such as a sternum retractor.

Preferably, the surgical deflector tool further comprises an elongated connection member cooperating with said deflection member and adapted for connection to said surgical platform.

The connection member enables the deflection member to be placed in a given desired position or orientation with respect to the surgical platform. In a variant, the position and orientation may be selected from among a plurality of possibilities.

The connection member advantageously comprises a first end portion connected to said deflection portion, and a second end portion, adapted for connection to said surgical platform.

This first example of connection member tends to be relatively simple, reliable and cost effective.

The connection member may be telescopic.

This example provides a connection member that is collapsible or extendible to a variable length, before or during a surgical intervention. As such, this example tends to offer compact deployment, flexibility in the surgical set-up, and ease of in-process re-adjustments, if required.

In another example, the connection member is flexible and lockable so that its configuration may be easily modified to enable requisite placement of the deflection member in various positions and/or orientations within the surgical workspace at which point the desired configuration may be locked during a surgical intervention.

The connection member may slidingly engage with said surgical platform. The connection member may slidingly engage with said deflection member.

These two examples provide variability in setting the position of the deflection member relative to the surgical platform.

The said deflection member may be pivotingly connected to said connection member.

This type of joint between the deflection member and connection member advantageously provides the surgeon with the ability to place the deflection member in an optimum orientation with respect to the surgical platform given a specific patient anatomy. In a variant, the orientation of deflection member may be selected from among a plurality of possibilities.

The surgical deflector tool of the invention preferably comprises an adjustment mechanism adapted to set said deflector member in a plurality of locations and/or orientations (angular settings) with respect to said surgical platform.

The adjustment mechanism enables the surgeon or assistant to easily and quickly position or orient the deflection member at the beginning of a surgical intervention and/or at any time during or after such intervention. This allows a surgeon to easily customize a surgical set-up and/or modify said set-up during the course of a surgery. Moreover, this allows the surgeon to easily vary the amount of deflection imposed by the surgical deflector tool on the engaged tissue retraction means during the course of a surgery without having to disengage deflection means from said surgical platform and/or without having to disengage tissue retraction means from said body tissue.

The connection member advantageously comprises a securing mechanism, capable of being fixed in a plurality of locations to said surgical platform.

The securing mechanism is advantageously adapted for sliding engagement with said surgical platform.

In various examples, the connection member is flexible and/or substantially arcuate. It is advantageously adapted to be slidingly engaged with said surgical platform. It is advantageously pivotingly connectable to said surgical platform.

Depending on the type of surgery to be performed, the patient's specific anatomy, the surgeon's distinct work preferences, and other related parameters, the ability to place the connection member in as many positions, orientations, or locations relative to the surgical platform offers advantages in being able to optimize the surgical approach during a surgical intervention.

In a preferred example, the deflection member is substantially elongated. An elongated profile enables the simultaneous deflection of a plurality of tissue retraction means.

In another example, the surgical deflector tool comprises two securing mechanisms, said deflection member comprising a deflection member spanning at least the distance between said two securing mechanisms, said deflection member rigidly engaged to at least one said securing mechanism. The deflection member may be pivotingly engaged to one securing mechanism and slidingly engaged to the other securing mechanism, or it may also be rotatingly engaged with both securing mechanisms, said deflection member capable of being fixed in a plurality of angular orientations relative to said securing mechanisms by action of said adjustment mechanism.

In a further example, the surgical deflector tool comprises a plurality of securing mechanisms each having a flexible portion, said deflection member comprising a deflection member, said deflection member spanning at least the distance between each of the securing mechanisms in the said plurality, said deflection member rigidly engaged to at least one securing mechanism and slidingly engaged to the remainder of securing mechanisms in the plurality, said deflection member capable of being fixed in a plurality of lengths spanning between any two adjacent securing mechanisms by action of said adjustment mechanism.

The invention also provides a surgical deflector tool comprising a deflection member and a securing mechanism, for deflecting at least a portion of a tissue retraction means, said tissue retraction means simultaneously engaged with a body tissue anatomically attached to a body organ and with a substantially stable surgical platform, said securing mechanism slidingly engaged with said surgical platform, said securing mechanism capable of being fixed in a plurality of locations to said surgical platform, said deflection member engaged with said tissue retraction means, said deflection member serving to deflect at least a portion of said tissue retraction means in a direction substantially away from the surface of said organ relative to its initial position with respect to said organ prior to engagement of said deflection member with said tissue retraction means.

In a variant, the surgical deflector tool further comprises an adjustment mechanism, said deflection member slidingly engaged with said securing mechanism, said deflection member capable of being fixed in a plurality of locations to said securing mechanism by action of said adjustment mechanism.

The invention also provides a surgical deflector tool comprising a deflection member and two securing mechanisms, for deflecting at least a portion of a tissue retraction means, said tissue retraction means simultaneously engaged with a body tissue anatomically attached to a body organ and with a substantially stable surgical platform, said securing mechanisms slidingly engaged with said surgical platform, said securing mechanisms capable of being fixed in a plurality of locations to said surgical platform, said deflection member engaged with said tissue retraction means, said deflection member serving to deflect at least a portion of said tissue retraction means in a direction substantially away from the surface of said organ relative to its initial position with respect to said organ prior to engagement of said deflection member with said tissue retraction means, said deflection member spanning at least the distance between said two securing mechanisms, said deflection member rigidly engaged to at least one said securing mechanism.

The deflection member may be pivotingly engaged to one securing mechanism and slidingly engaged to the other securing mechanism.

The tool preferably further comprises an adjustment mechanism, said deflection member rotatingly engaged with said securing mechanism, said deflection member capable of being fixed in a plurality of angular orientations relative to said securing mechanism by action of said adjustment mechanism.

The invention also provides a surgical deflector tool comprising a deflection member, an adjustment mechanism and two securing mechanisms, for deflecting at least a portion of a tissue retraction means, said tissue retraction means simultaneously engaged with a body tissue anatomically attached to a body organ and with a substantially stable surgical platform, said securing mechanisms slidingly engaged with said surgical platform, said securing mechanisms capable of being fixed in a plurality of locations to said surgical platform, said deflection member engaged with said tissue retraction means, said deflection member serving to deflect at least a portion of said tissue retraction means in a direction substantially away from the surface of said organ relative to its initial position with respect to said organ prior to engagement of said deflection member with said tissue retraction means, said deflection member spanning at least the distance between said two securing mechanisms, said deflection member rotatingly engaged with both securing mechanisms, said deflection member capable of being fixed in a plurality of angular orientations relative to said securing mechanisms by action of said adjustment mechanism.

The invention further provides a surgical deflector tool comprising a deflection member, an adjustment mechanism and a plurality of securing mechanisms, for deflecting at least a portion of a tissue retraction means, said tissue retraction means simultaneously engaged with a body tissue anatomically attached to a body organ and with a substantially stable surgical platform, said securing mechanisms slidingly engaged with said surgical platform, said securing mechanisms capable of being fixed in a plurality of locations to said surgical platform, said securing mechanism having a flexible portion, said deflection member engaged with said tissue retraction means, said deflector serving to deflect at least a portion of said tissue retraction means in a direction substantially away from the surface of said organ relative to its initial position with respect to said organ prior to engagement of said deflection member with said tissue retraction means, said deflection member spanning at least the distance between each of the securing mechanisms in the said plurality, said deflection member rigidly engaged to at least one securing mechanism and slidingly engaged to the remainder of securing mechanisms in the plurality, said deflection member capable of being fixed in a plurality of lengths spanning between any two adjacent securing mechanisms by action of said adjustment mechanism.

These and other objects of the present invention will become apparent from the description of the present invention and its preferred embodiments which follows.

BRIEF DESCRIPTION OF THE DRAWINGS

For better understanding of the present invention and to show more clearly how it may be carried into effect, reference will now be made by way of illustration and not of limitation to the accompanying drawings, which show an apparatus according to the preferred embodiments of the present invention, and in which:

FIG. 9A is a top view illustrating a surgical deflector tool and a surgical apparatus with which the said surgical deflector tool may be used, according to a fourth embodiment of the present invention;

FIG. 9B is a section view through the surgical deflector tool illustrated in FIG. 9A, illustrating a pivot-type support frame of said surgical deflector tool;

FIG. 9C is a section view through the surgical deflector tool illustrated in FIG. 9A, illustrating a yoke-type support frame of said surgical deflector tool;

FIG. 10A is a top view illustrating a surgical deflector tool and a surgical apparatus with which the said surgical deflector tool may be used, according to a fifth embodiment of the present invention;

FIG. 10B is a side elevational view through the surgical deflector tool illustrated in FIG. 10A, illustrating a louver-type deflector of said surgical deflector tool;

FIG. 10C is a section view through the surgical deflector tool illustrated in FIG. 10B, illustrating an adjustment mechanism of said surgical deflector tool;

FIG. 11A is a top view illustrating a surgical deflector tool and a surgical apparatus with which the said surgical deflector tool may be used, according to a sixth embodiment of the present invention;

FIG. 11B is a section view through the surgical deflector tool illustrated in FIG. 1I A, illustrating a solid-flange support frame of said surgical deflector tool;

FIGS. 11C and 11D are section views through the surgical deflector tool illustrated in FIG. 11A, illustrating sliding-flange support frames of said surgical deflector tool;

FIG. 11E is a section view through the surgical deflector tool illustrated in FIG. 11A, illustrating a support frame with integral housing for adjustment mechanism of said surgical deflector tool;

DETAILED DESCRIPTION OF THE INVENTION

The features and principles of this invention can be applied, in whole or in part, to other types of cardiac surgery or other surgery whereby a body organ is positioned or oriented through the retraction of a body tissue anatomically attached to said body organ, and the setting of a desired position or orientation of said body organ is achieved through the securing of the retraction load relative to a substantially stable surgical platform. The embodiments of the present invention that follow will however be described and illustrated in the context of cardiac surgery, and more specifically, CABG surgery.

In part, the embodiments of this invention may be advantageously applied, if desired, to the chest retractor described in copending Canadian patent application Serial No. 2,216,893 filed on Sep. 30, 1997 in the names of Cartier and Paolitto and entitled "Sternum Retractor for Performing Bypass Surgery on the Beating Heart" and in copending Canadian patent application Serial No. 2,237,877 filed on Jun. 26, 1998 in the names of Paolitto et al. and entitled "Chest Retractor for Performing Cardiac Surgery", for which a corresponding PCT application Serial No. PCT/CA99/00593 has been filed on Jun. 25, 1999 in the names of Paolitto et al. and entitled "Surgical Retractor Having Low-Friction Actuating Means and Contoured Blade Arms", the contents of which are incorporated herein by reference. Alternatively, the embodiments of the invention may also be applied to other types of chest retractors capable of securing a surgical deflector tool according to the present invention in a substantially stable orientation and position relative to the chest retractor. Alternatively, the chest retractor may be replaced by other substantially stable surgical platforms that may be engaged with a surgical deflector tool according to the present invention. Such surgical platforms would include: a surgical table, a surgical bridge or truss or truss member attached to a surgical table and spanning the patient or set adjacent to the patient, or other like platforms.

In part, the embodiments of this invention may be advantageously applied, if desired, to the tissue retractor described in above referenced Canadian patent application Serial No. 2,242,295 for which a corresponding PCT application Serial No. PCT/CA99/00740 has been filed, the contents of which are incorporated herein by reference.

Figure 1:
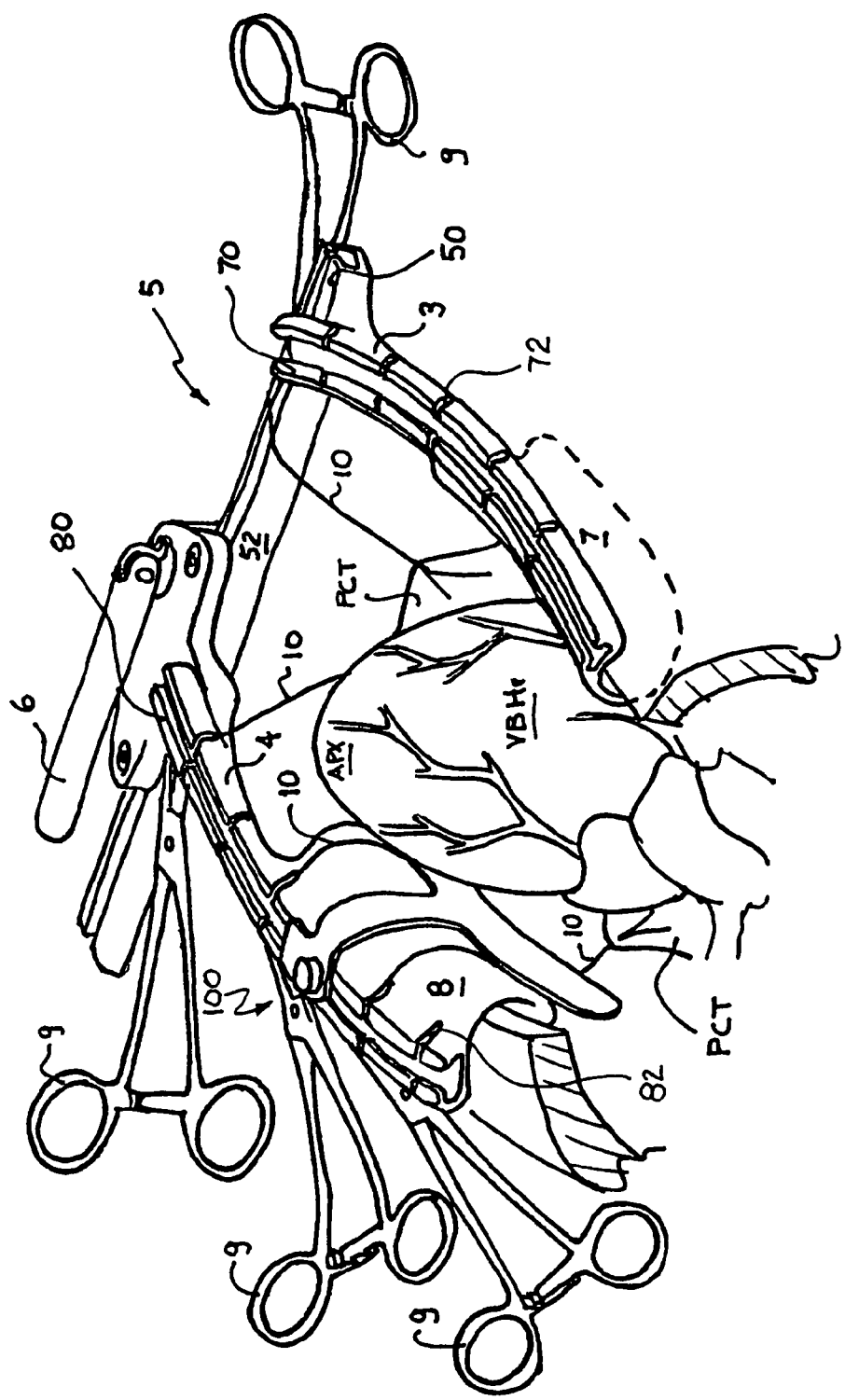
FIG. 1 is a perspective view illustrating a surgical deflector tool and a surgical apparatus with which the said surgical deflector tool may be used, according to a first embodiment of the present invention.

By way of a general overview and with reference to FIG. 1, a surgical apparatus with which the invention may be used is comprised of three main components, a surgical deflector tool 100, a tissue retraction means in the nature of a surgical suture 10, and a chest retractor such as sternum retractor 5. The sternum retractor 5 is illustrated in its deployed state, thereby creating and maintaining a surgical window that provides the surgeon with access to the patient's cardiac tissue. During the course of a cardiac surgery, a surgeon needs to perform certain tasks within a surgical workspace. This surgical workspace is defined by an area that contains the perimeter of a deployed sternum retractor 5 and a buffer zone therebeyond, and said area extending below to the depth of the patient's thorax, and above to the height above the retracted chest cavity in which the surgical apparatus comprising the surgical deflector tool is contained and manipulated.

The sternum retractor 5 includes four major parts: (i) an elongated rack bar 52, (ii) a first retractor spreader arm 3 being preferably fixed to the rack bar 52, (iii) a second retractor spreader arm 4 being preferably movable with respect to the rack bar 52, and (iv) an crank handle 6 for effecting movement of the retractor spreader arm 4 relative to retractor spreader arm 3.

Retractor spreader arms 3 and 4 extend in a direction substantially transversely with regard to the rack bar 52, generally in the same direction therefrom and in a parallel orientation with respect to one another. The movable arm 4 can be displaced along the rack bar 52, and relative to the other arm 3, preferably through the rotation of the crank handle 6 activated by the surgeon. The crank handle 6 is operatively connected to the rack bar 52 and to the other spreader arm 4, and is translatable along the length of the rack bar 52. This is preferably achieved by the engagement of a pinion mechanism (not shown) of crank handle 6 with the rack teeth on rack bar 52. Two retractor blades 7 and 8 are respectively provided with the retractor spreader arms 3 and 4, preferably disposed below the rack bar 52 when the sternum retractor 2 is deployed on a patient. The retractor blades 7 and 8 engage with and serve to retract a portion of the patient's incised skin, the two halves of the patient's incised sternum and the patient's ribcage thereby exposing the cardiac tissue to be operated on through the resultant surgical window. When viewing the resultant surgical window from above the patient, the retractor arms 3 and 4 of the deployed sternum retractor 5 each have a generally arcuate orientation.

The sternum retractor 5 advantageously comprises arcuate rails 70 and 80 along the top of arcuate retractor spreader arms 3 and 4, respectively. The rails 70 and 80 configure an inverted T-slot arcuate passage 71 and 81, respectively, preferably centrally located within said rails, and preferably extending throughout the entire arcuate length of said rails. A similar linear longitudinal rail 50, may also be configured along the top of rack bar 52. Longitudinal rail 50 is also configured with an inverted T-slot longitudinal passage 51, preferably extending throughout its entire longitudinal length. These said rails form a mounting perimeter that can advantageously serve to engage a surgical deflector tool 100 in a variety of substantially stable positions and orientations within a surgical workspace. As well, these rails can also be utilized to engage other surgical apparatus, that may need to be secured along the perimeter of the sternum retractor 5 during cardiac surgery. For instance, these rails may advantageously serve to engage a positioning and articulation mechanism utilized to place a variety of heart stabilizers during beating heart bypass surgery, for instance, as described in previously mentioned Canadian application Serial No. 2,216,893. Alternatively, the positioning and articulation mechanism may also be utilized to set a cardiac tissue contacting member used in cardiac surgery, such as a valve tissue retractor for example. As well, these rails can also be utilized to engage other surgical apparatus, that may need to be secured along the perimeter of the sternum retractor 5 during cardiac surgery.

A plurality of slit-like channels 72 and 82 are configured along the arcuate arms 3 and 4 and cut through arcuate rails 70 and 80, respectively. FIG. 1 illustrates a plurality of such slit-like channels 72 on the retractor spreader arm 3 and a plurality of such slit-like channels 82 on the retractor spreader arm 4. The slit-like channels 72 and 82 extend downwards from the top of the rails 70 and 80 to a depth preferably below the entire depth of the inverted T-slot arcuate passages 71 and 81, preferably by an amount equivalent to the width of said slit-like channel. Similar slit-like channels were introduced in above-mentioned Canadian patent application Serial No. 2,242,295 in order to provide passages for the placement of sutures serving to retract body tissue, for example pericardium tissue. These said slit-like channels are configured so that a suture line or other like wire-like filament will not restrict or otherwise hinder the functionality of a surgical deflector tool or a positioning and articulation mechanism when such devices becomes engaged in said passages 71 and 81 of said rails 70 and 80, provided the suture line or other wire-like filament is placed in the deepest position within said slit-like channel.

FIG. 1 illustrates an example of one possible surgical set-up whereby the patient's heart is verticalized through pericardial retraction, prior to possibly performing beating heart bypass graft surgery on a posterior or inferior coronary artery. Coronary stabilizers that may be used to immobilize a portion of the beating heart surface around the target artery requiring grafting are not shown. In this example, four tissue retraction means in the nature of a surgical suture 10 are used to apply pericardial traction to the patient's incised pericardium tissue (labelled as PCT). Once the desired pericardial retraction load is applied to each surgical suture 10, both ends of the surgical suture are inserted into one of slit-like channels 82 (or 72 in other surgical set-ups), and the desired retraction load is maintained by securing the two ends of the surgical suture 10 relative to sternum retractor 5 with surgical clamp 9. Alternatively, both ends of a surgical suture 10 may also be placed over rack bar 52 and in between two rack bar teeth (not shown), and secured relative to said rack bar by a surgical clamp 9. As such, the longitudinal axis of the heart assumes a substantially vertical orientation with the apex (labelled as APX) of the verticalized beating heart (labelled as VBH) resting substantially proud above the plane formed through the top of deployed sternum retractor rails 70 and 80. In this example, the patient is placed in a substantially horizontal supine position on a surgical table. In this example, rack bar 52 is placed towards the patient's feet. As illustrated, the anterior coronary arteries are most visible. The surgical deflector tool 100 is subsequently deployed.

Figure 2:
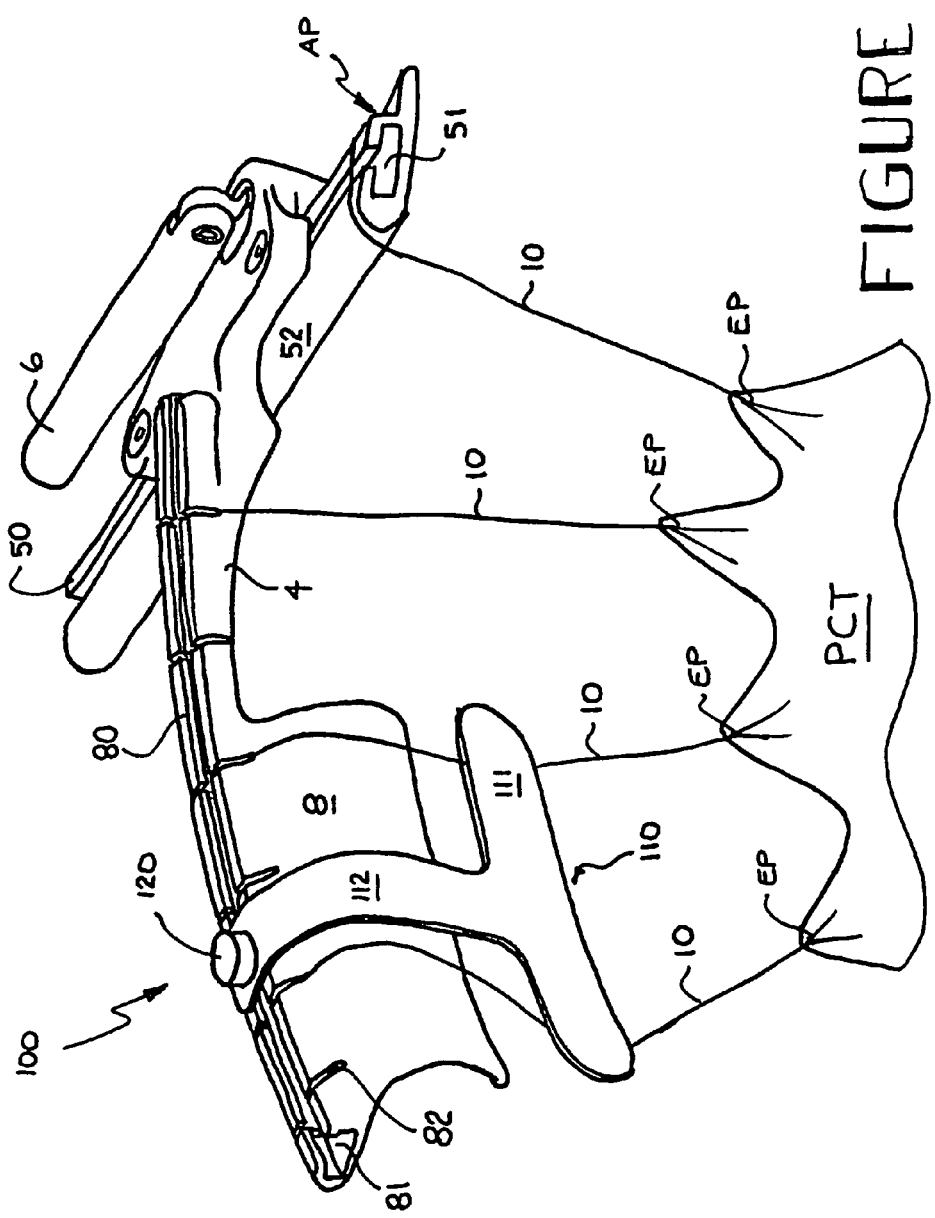
FIG. 2 is an enlarged perspective view of the surgical deflector tool illustrated in FIG. 1, with the verticalized beating heart removed for clarity.
Figure 3:
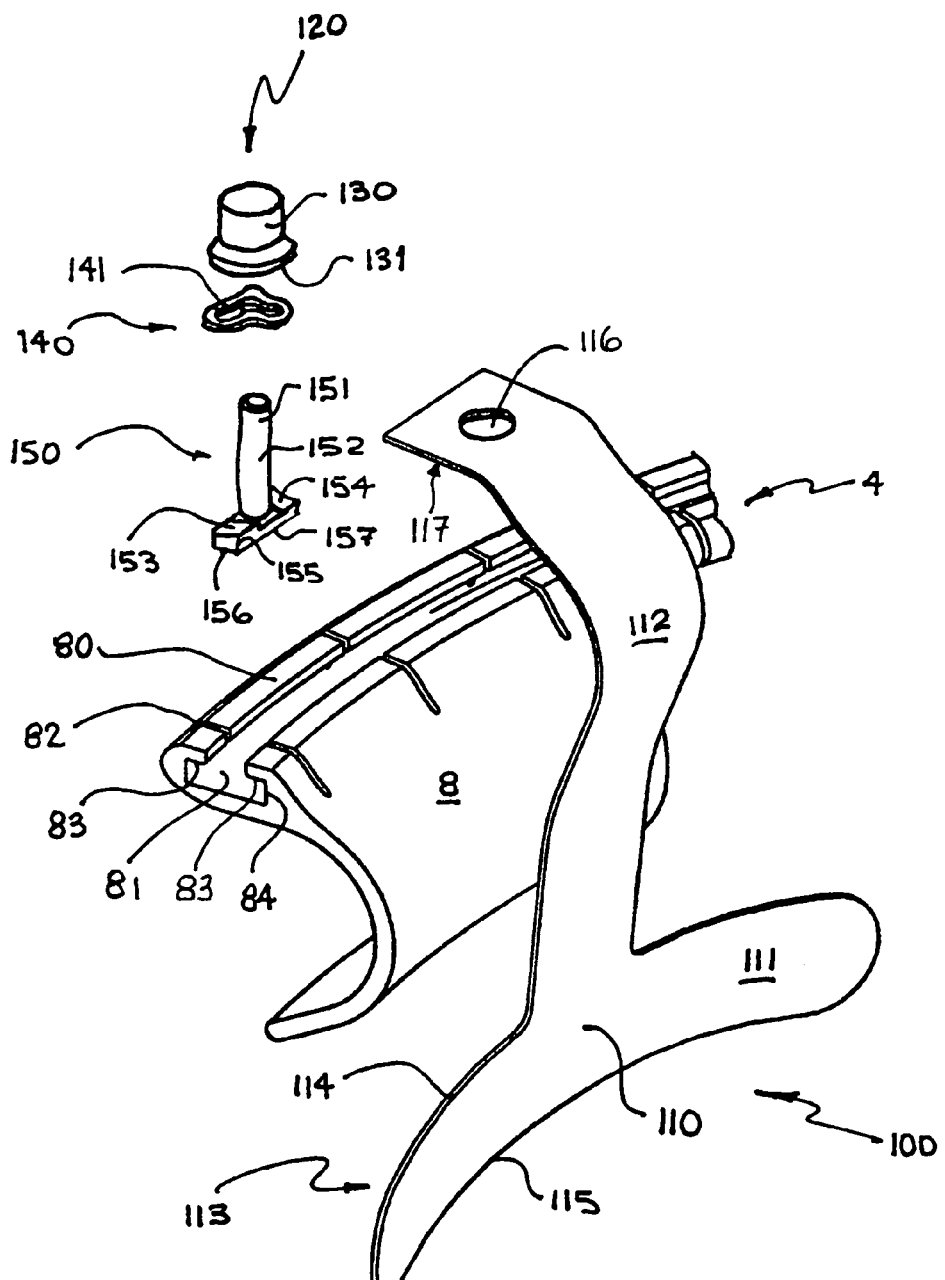
FIG. 3 is an exploded view of the surgical deflector tool illustrated in FIG. 1.
Figure 12A:
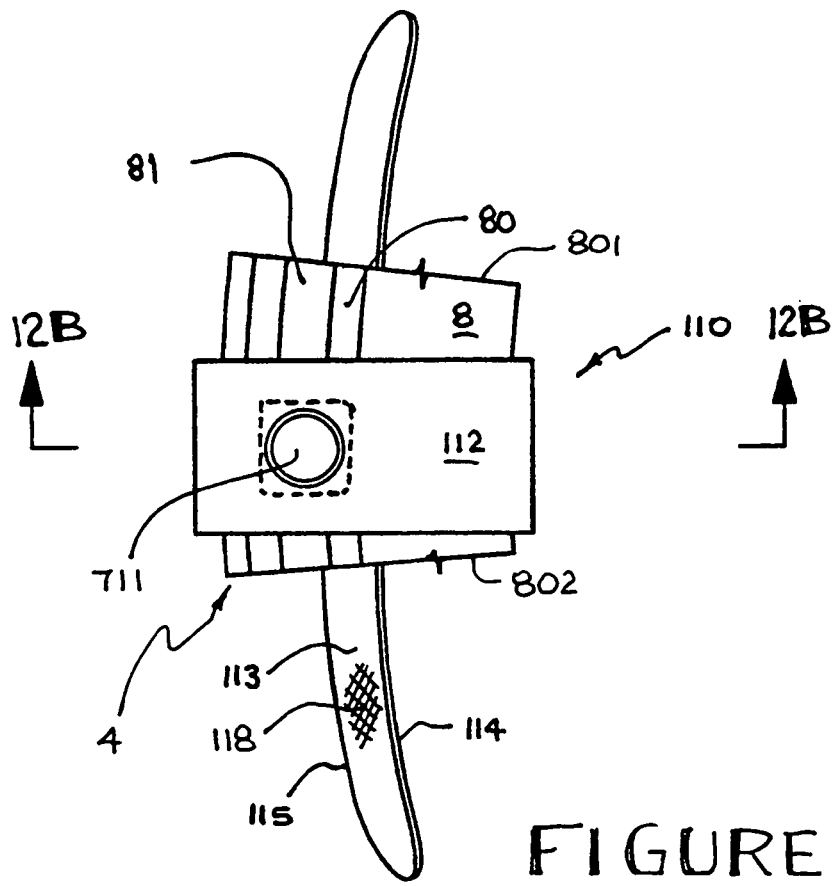
FIG. 12A is a top view illustrating a variant securing mechanism in the nature of a T-nut, according to the present invention.
Figure 12B:
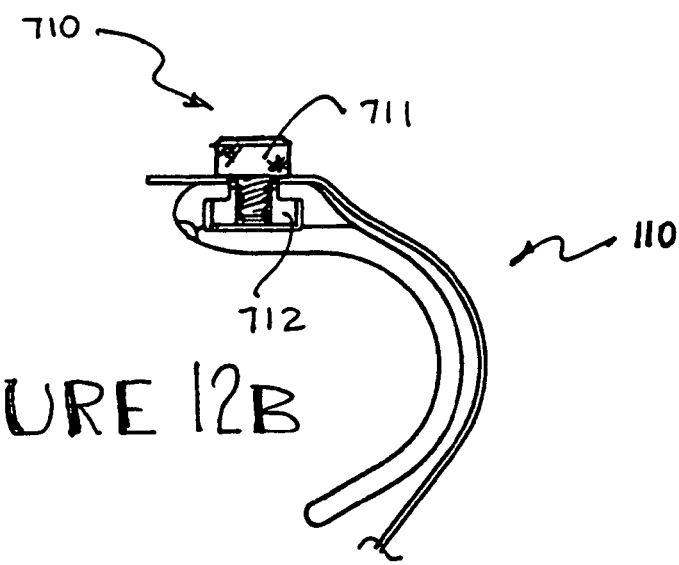
FIG. 12B is a section view through the variant securing mechanism illustrated in FIG. 12A.

As further illustrated in FIGS. 2 and 3, a first embodiment of a surgical deflector tool 100 according to the present invention is comprised of a sheet-like deflector baffle 110 and a securing mechanism in the nature of a cam assembly 120. Surgical deflector tool 100 is capable of simultaneously engaging more than one surgical suture 10, for example as illustrated in FIG. 2, two such surgical sutures 10. Sheet-like deflector baffle 110 is configured in an inverted T-shape profile. The longitudinal axis of horizontal elongate deflection member 111 of the inverted T-shape is formed in a substantially arcuate shape of similar curvature to the arc of the retractor spreader arm 8 when said retractor spreader arm is viewed from above the surgical window. The longitudinal axis of the vertical connection member 112 of inverted T-shape is also bent in a substantially arcuate shape to conform closely to the shape and curvature of blade 8 so as to create the minimum obstruction within the surgical window when said deflector tool 100 is in use and engaged with sternum retractor 5. When the surgical deflector tool 100 is deployed and secured to the retractor spreader arm 4 such that cam assembly 120 is in a location along arcuate rail 80 approximately mid way between the lateral ends of arcuate blade 8, at least a portion of horizontal deflection member 111, and more specifically at least a portion of its contours 114 and 115, are preferably tucked below blade 8 and laterally outward away from the verticalized beating heart VBH. When viewed from above the surgical window, at least a portion of said deflection member 111 would not be visible since it is hidden by blade 8 and in a position laterally outward beyond the retracted sternum half. This is further illustrated in FIG. 12A with cam assembly 120 replaced by a variant securing mechanism in the nature of T-nut assembly 710. In FIG. 12A, only a portion of retractor arm 4 and blade 8 is shown between break lines 801 and 802.

Cam assembly 120 is comprised of a clamping knob 130, a wave spring washer 140, and a cam 150. The mechanical assembly of surgical deflector tool 100 consists of inserting cam shaft 152 of cam 150 through hole 116 in baffle 110 and subsequently through hole 141 in wave spring 140. Cam shaft end 152 is then rigidly engaged with knob 130 either through a press fit, or secured by a set screw (not shown), or by brazing, or by other like means. Once mechanically assembled, the cam 150 and knob 130 are free to rotate relative to baffle 110 and wave spring 140.

Cam 150 is configured with two diametrically opposite ramp-like cam surfaces 153, 154. The narrower width 156 of cam 150 allows it to be inserted within passage 81 (or 71 or 51) when its length 157 is aligned substantially tangent to the longitudinal axis of said passage. Once cam 150 is inserted within said passage, face 117 of baffle 110 rests on top of rail 80 (or 70, or 50), and deflection member 111 becomes engaged with and deflects one or more surgical sutures 10 that come in contact with its contact surface 113 during use. A clockwise rotation of knob 130 will simultaneously rotate into engagement the ramp-like surfaces 153, 154 of cam 150 with faces 83 of arcuate passage 81. Similar faces to face 83 exist in longitudinal passage 51. Height 155 of cam 150 is inferior to height 84 of passage 81 to allow free rotation of said cam within said passage 81 (71 or 51) and, when installed, to not interfere with surgical sutures 10 that may be placed within slit-like channels 82 (or 72). Clockwise rotation of knob 130 engages cam surfaces 153, 154 to faces 183 of passage 81 thereby causing wave spring 140 to be progressively compressed and flattened thereby exerting a clamping load on baffle 110 in the vicinity of perimeter of hole 116. Once engaged, cam shaft 152 is in tension while baffle 110, wave spring 140 and rail 80 are in compression and clamped between knob face 131 and a portion of ramp-like cam surfaces 153, 154. Counterclockwise rotation of knob 130 disengages the cam surface 153, 154 and relieves the clamping load. As such, surgical deflector tool 100 is slidingly engaged within passage 81 (or 71 or 51) and may be repositioned in-process along the entire length of rail 80 (or 70 or 50) without withdrawal of cam assembly 120 from within passage 81 (or 71 or 51).

A texture may be configured on the contact surface 113 of baffle 110 to tend to improve adherence between surgical suture 10 and said contact surface 113 when the surgical deflector tool 100 is deployed (or when applicable, between retracted pericardium tissue PCT in the vicinity of surgical suture 10 and said contact surface 113). Said texture may be provided in the nature of gradual ridges, depressions, dimples, channels, grooves or other like features disposed on at least a portion of contact surface 113. This texture is schematically represented in FIG. 12A as feature 118 on a portion of contact surface 113 of baffle 110. Alternatively, said texture may also be comprised of a biocompatible hydrogel coating or friction-enhancing polymer or elastomer. If advantageous, this said texture may be configured on the contact surfaces of other deflection members described in other embodiments or variant according to the present invention.

In another example of a usage of the surgical deflector tool 100 according to this first embodiment of the present invention, the surgical deflector tool 100 may be used without tissue retraction means. In this method of use, the surgical deflector tool 100 serves the purpose of deflecting or constraining the patient's expanding breathing lung in a position away from the patient's heart thereby tending to improve the surgical access and surgeon visibility to the patient's heart during a cardiac surgical intervention and tending to avoid the need for lung deflation to increase surgical access. This also tends to avoid the need for assistant-hand-held tissue retractors in order to obtain the desired surgical access.

Figure 4:
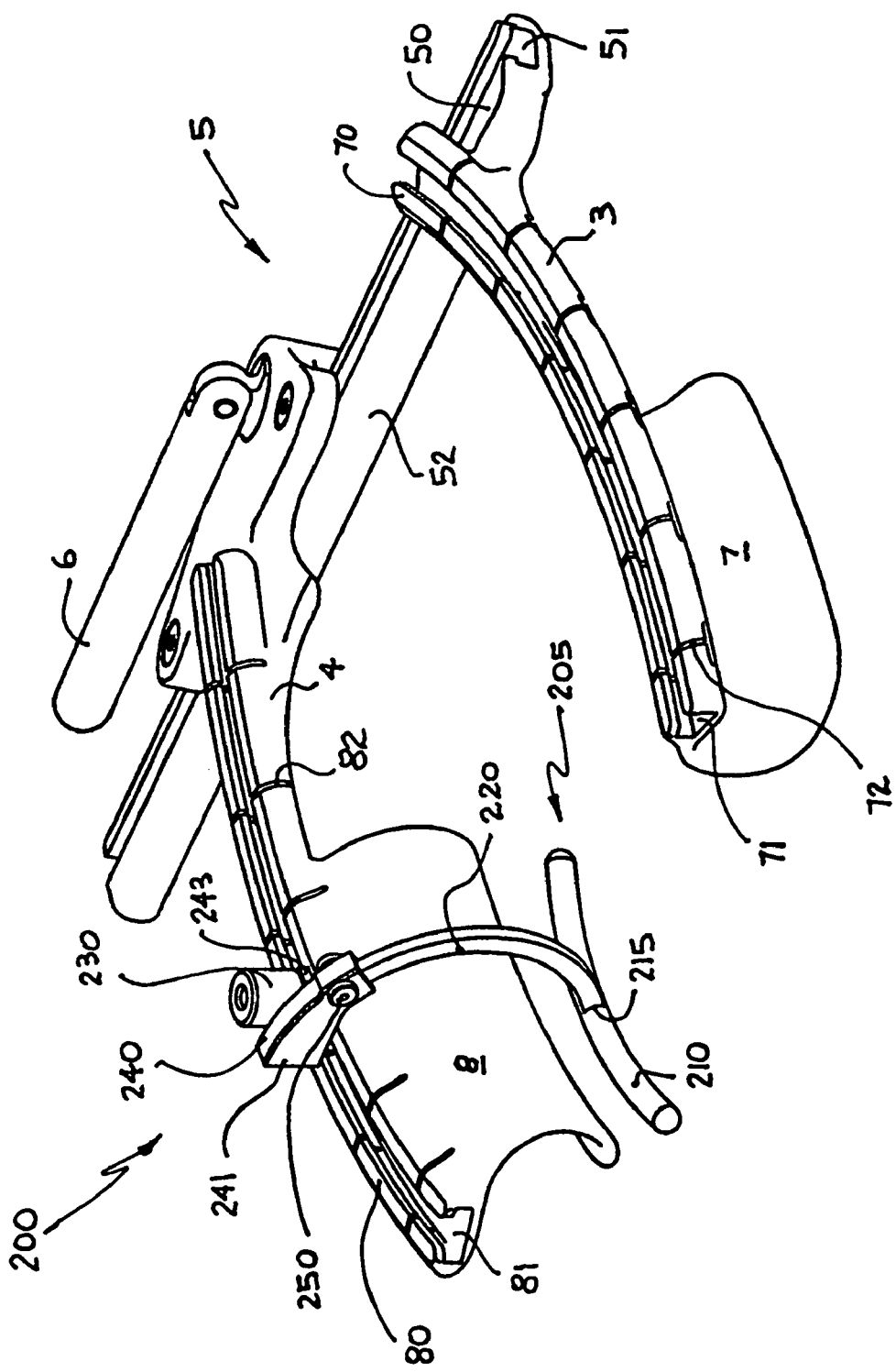
FIG. 4 is a perspective view illustrating a surgical deflector tool and a surgical apparatus with which the said surgical deflector tool may be used, according to a second embodiment of the present invention.
Figure 5:
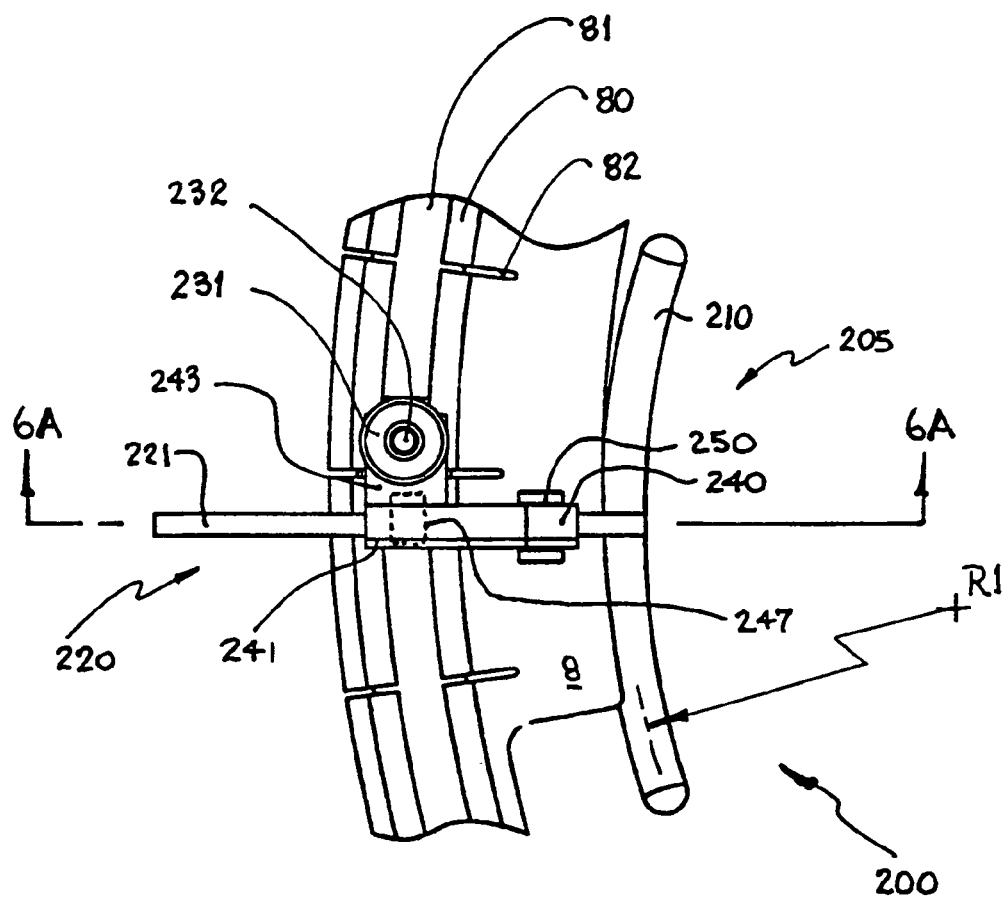
FIG. 5 is an enlarged top view of the surgical deflector tool illustrated in FIG. 4.

FIGS. 4–6 illustrate a second embodiment according to the present invention. A surgical deflector tool 200 is comprised of a rod-like deflector 205, a securing mechanism in the nature of a threaded clamp 230, and an adjustment mechanism in the nature of a wedge pin assembly 250.

Rod-like deflector 205 consists of a substantially arcuate elongate deflection member 210 and arcuate connection member 220, joined in substantially perpendicular end-to-side mechanical joint 215. Mechanical joint 215 is preferably rigid. It may form a permanent assembly between members 210 and 220 such as may be achieved through a weldment, a brazed joint, or other like means. Alternatively, it may form a demountable joint such as may be achieved through a threaded interface, bolted assembly, riveted assembly, or other like mechanical joining means. The horizontal-spanning deflection member 210 is configured with a substantially circular cross section and radius of curvature R1. The vertical-spanning connection member 220 is illustrated with a substantially rectangular cross-section and radius of curvature R2. The cross-section profile of connection member 220 is configured with at least a flat portion along outboard substantially cylindrical surface 221 serving as a rolling surface suitable for engagement with wedge pin 251. The remaining cross-section profile of member 220 will be slightly inwardly offset from the mating cross-section profile of housing passage 246 through housing 240 to create a slight clearance that allows relatively free arcuate translation of member 220 through housing 240 when wedge pin 251 is disengaged from contact with either outboard surface 221 or wedge surface 245 in housing 240. These said cross-section profiles must be such to achieve anti-rotation of cross-section of member 220 relative to cross-section of housing passage 246.

Housing 240 is configured with two passages, one in the form of a hole to engage with threaded clamp 230, the other in the form of an arcuate housing passage 246 to engage rod-like deflector 205. Arcuate passage 246 and wedge surface 245 are machined out of housing 240 and preferably permanently capped by face plate 241. Once housing 240 and face plate 241 are assembled, wedge pin 251 is inserted through an opening in housing 240, transverse to arcuate passage 246, and through a similar opening in face plate 241 that is in-line with opening in housing 240. Wedge pin 251 is configured with two actuation wheels 252, 253. One actuation wheel 252 may be integral to wedge pin 251 while the opposing actuation wheel 253 is engaged with wedge pin 251 only after said wedge pin is inserted through openings in housing 240 and face plate 241. Wedge pin 251 is thereby slidingly and rotatingly engaged with housing 240.

Flat face 280 on housing 240 rests atop of the arcuate rail 80 (or 70 or 50) when the surgical deflector tool 200 is secured relative to sternum retractor 5. Flat face 280 is offset towards bottom of arcuate passage 80 to create substantially rectangular-sided anti-rotation island or dog 247 which is inserted between lateral faces of passage 80 (or 70 or 50). Anti-rotation dog 247 maintains longitudinal axis of connection member 220 in a substantially perpendicular orientation to arcuate rail 80 and provides the anti-rotation feature to react the tightening torque applied to knob 230. Flat face 280 is offset upwards away from arcuate passage 81 to define face 242. Resulting thickness between face 242 and 280 defines flange 243 through which a hole is machined to engage threaded clamp 230.

Threaded clamp 230 is comprised of a threaded knob 231, and clamping plate 233 with integral threaded shaft 232. Threaded shaft 232 is inserted through hole in flange 243 and engaged with threaded knob 231 to form a demountable mechanical assembly. Clamping plate 233 is configured with dimensions that allow it to slide freely, together with surgical deflector tool 200, through passage 81 (or 71 or 51) when threaded knob 231 is not tightened. Clamping plate 233 is preferably configured with a rectangular profile when viewed along the axis of threaded shaft 232. The narrower width of this rectangular profile is slightly smaller than the width of passage 80 (or 70 or 50) at its narrowest topmost location. The longer width of this rectangular profile is slightly longer than the width of passage 80 (or 70 or 50) at its widest bottommost location. This allows the clamping plate 233 to be inserted into passage 80 by vertically bringing into contact face 280 of surgical deflector tool 200 with rail 80 of sternum retractor 5 when narrower width of said rectangular profile is aligned with width of said passage 80. With face 280 in contact with top face of rail 80, a rotation of threaded knob 231 may at first rotate threaded shaft 232 until clamping plate 233 is rotated into contact with the sides of passage 80 thereby providing an antirotation feature allowing the further rotation of knob 231 to apply a clamping load across flange 243 and rail 80. At this point, surgical deflector tool 200 is secured relative to sternum retractor 5. Other variants for a securing mechanism in the nature of a threaded clamp are possible and will be described more fully below.

Figure 6A:
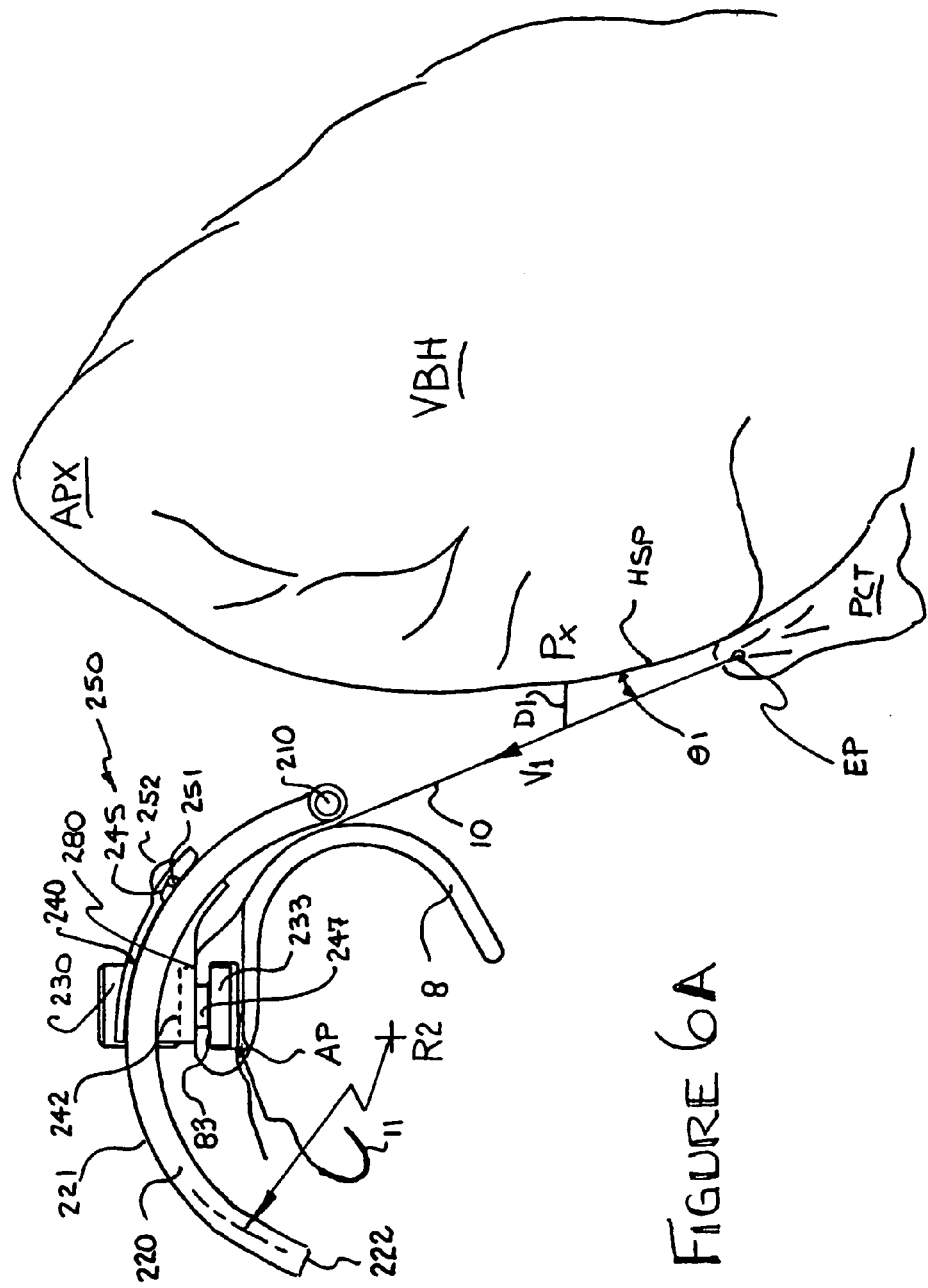
FIG. 6A is a section view through the surgical deflector tool illustrated in FIG. 5, illustrating said deflector tool in its non-deployed state.

FIG. 6A illustrates surgical deflector tool 200 secured to sternum retractor 5, with its deflection member 210 in slight contact with a tissue retraction means in the nature of surgical suture 10, but prior to the deployment of the surgical deflector tool 200. This is referred to as the initial, non-deployed configuration of said deflector tool. The tensile retraction load exerted on the PCT by the surgical suture 10 is secured relative to sternum retractor 5 by surgical clamp 9 (not shown in FIGS. 6A–6B) at a suitable anchoring point (labeled AP). As such, said suture 10 is in tension by virtue of its simultaneous engagement with retracted pericardium tissue PCT and said sternum retractor. To deploy surgical deflector tool 200, the surgeon applies a manual push load at proximal end 222 of arcuate connection member 220, thereby causing a clockwise arcuate translation of said member 220 through passage 246 of housing 240. As a result, deflection member 210 will apply a deflection load to at least one surgical suture 10. As deflection member 210 tries to deflect surgical suture 10, the tissue retraction load which the said surgical suture is already applying to the PCT will tend to resist said deflection and want to rotate in an opposing counterclockwise rotation member 220 through housing 240 when the said surgeon-applied load is sufficiently decreased or removed. As such, when the surgeon releases proximal end 222, there will be a slight counterclockwise rotation of member 220 thereby entraining wedge pin 251 to substantially roll along outboard surface 221 of arcuate member 220 and become wedged between housing face 245 and said surface 221. This wedging action stops the counterclockwise arcuate translation of said member 220 through said housing 240. Consequently, the position of rod-like deflection member 210 is set relative to housing 240 and sternum retractor 5, thereby also deflecting surgical suture 10 the desired amount. Clockwise and counterclockwise directions are defined relative to FIGS. 6A–6B.

During the course of a surgical intervention, if it is desired to increase the deflection on surgical suture 10 and extend arcuate rod 210 deeper into chest cavity and laterally outward below the patient's ribcage and away from VBH, a manual push load is re-applied to proximal end 222 to overcome the resistance load exerted by surgical suture 10 on deflection member 210. By this action, wedge pin 251 is un-wedged as it rolls over contact surface 221 allowing clockwise arcuate translation of member 220 relative to housing 240. Once the desired position is obtained, releasing proximal end 222 will cause a very slight counterclockwise arcuate translation of member 220 through housing passage 246 thereby re-engaging wedge pin 251 and re-securing the position of the deployed surgical deflector tool. During the surgical intervention, if it is desired to decrease the deflection on the surgical suture 10, actuation wheel 252 or 253 may be rotated by the surgeon, thereby un-wedging pin 251 between contact surfaces 245 and 221, and allowing the arcuate member 220 to be retracted through passage 246 of housing 240 in a counterclockwise direction. The surgical deflector tool 200 is capable of providing in-process readjustments to the deflection amount on the surgical sutures 10 that are engaged with said tool 200.

Figure 6B:
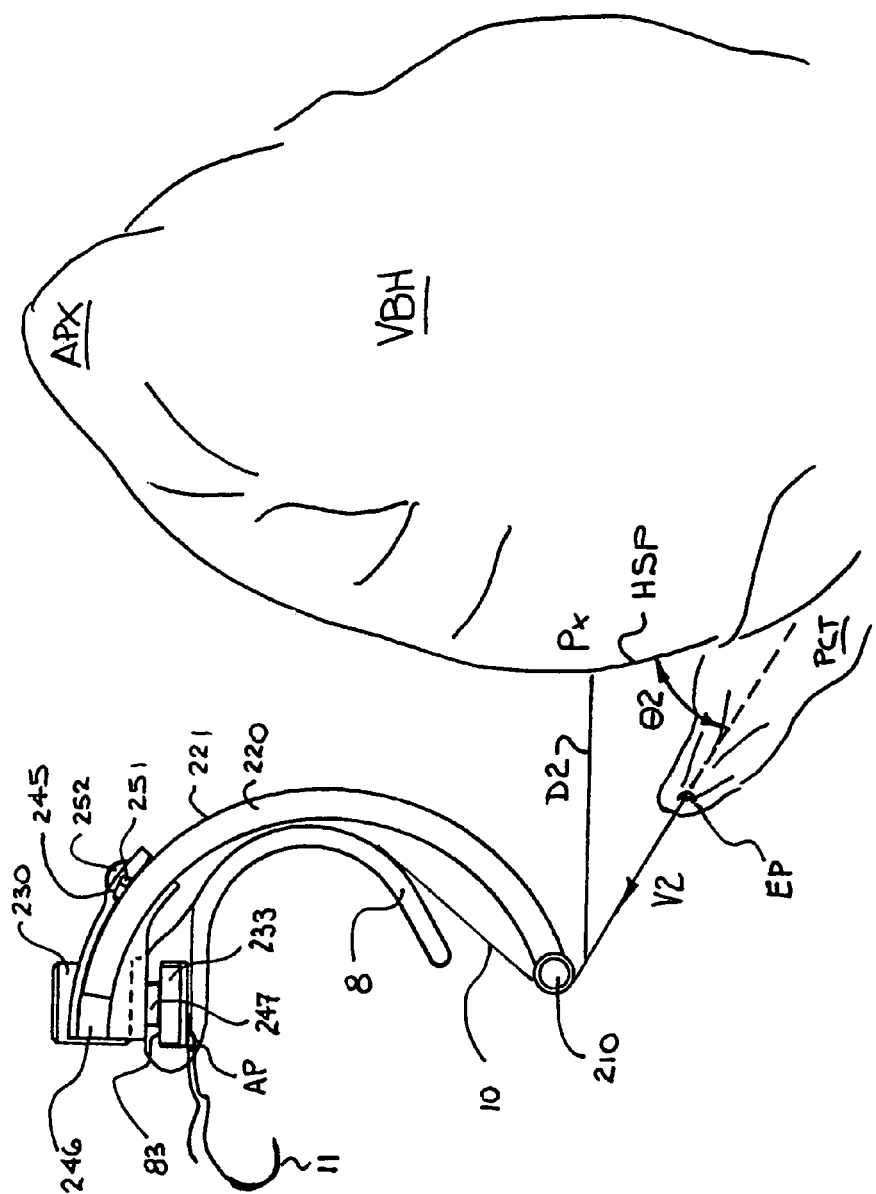
FIG. 6B is a section view through the surgical deflector tool illustrated in FIG. 5, illustrating said deflector tool in its deployed state.

FIG. 6B illustrates a deployed surgical deflector tool 200 secured to sternum retractor 5, with its deflection member 210 engaged with at least one surgical suture 10 and having deflected said suture 10 from its initial non-deflected position illustrated in FIG. 6A. This will be referred to as a deployed configuration of said surgical deflector tool.

Referring to FIG. 6A, Px depicts a target point on the verticalized beating heart VBH, in the general vicinity of where a surgical intervention is intended to take place. Distance D1 is a laterally projected distance between the target point Px and a surgical suture 10 applying pericardial traction. V1 is a vector emanating from the engagement point (labelled as EP) of the tissue retraction means on the pericardium tissue, in this example the piercing point of suture 10 through PCT. Vector V1 is directed along surgical suture 10 in a direction generally towards the anchoring point AP of said suture on chest retractor 5. $\theta1$ is an angle in the plane containing V1 and Px, between vector V1 and the heart surface profile HSP that is seen in said plane containing V1 and Px.

Often times in a retracted chest cavity, the laterally projected distance D1 may be small and restrictive for certain types of surgical interventions. For instance, in a beating heart revascularization of a posterior coronary artery, this distance D1 may be small or restrictive that it may hinder not only the deployment of a coronary stabilizer that serves to immobilize the portion of beating heart around the said posterior target artery in the vicinity of point Px, but it may also compromise the quality of the posterior artery bypass graft. The intended benefit that may be obtained by deploying a surgical deflector tool 200 is illustrated in FIG. 6B. This intended benefit also applies to other embodiments according to the present invention.

With the deployment of surgical deflector tool 200, vector V1 is redirected to become vector V2. Laterally projected distance D1 is increased to D2 as at least a portion of the surgical suture 10 engaged with the pericardium tissue is moved laterally away from the heart surface profile HSP at location of target point Px. Angle $\theta1$ also increases to $\theta_2$ as vector V1 is redirected to assume a more perpendicular orientation, V2, relative to the heart surface profile HSP. The increase in distance D1 to D2 tends to improve surgical access and surgeon's vision at the site of an intended surgical intervention in the vicinity of point Px. It also tends to facilitate the deployment of a coronary stabilizer and the posterior artery bypass grafting procedure. The surgical field in the vicinity of Px is thereby increased.

Depending on the magnitude of surgical suture deflection desired, the deployment of surgical deflector tool 200 may also assist in further verticalizing the apex APX of the heart, or cause a substantially clockwise rotation of the verticalized beating heart VBH tending to improve access to Px. This clockwise rotation is in reference to the FIGS. 6A and 6B.

In broad terms, a surgical procedure for a set-up and deployment of a surgical deflector tool 200 utilized in a beating heart CABG surgery, and relating to the present invention consists of:

(a) performing a full or partial midline sternotomy incision;

(b) cauterizing of any bleeding vessels subsequent to the sternotomy incision;

(c) if an internal thoracic artery (ITA) will be used as a bypass conduit, retracting the two halves of the patient's incised sternum with a surgical retractor suitable for exposing the ITA and the surgical harvesting thereof;

(d) retrieving the surgical retractor used for ITA harvesting, and inserting blades 7 and 8 of sternum retractor 5 along the sternotomy incision;

(e) retracting the patient's ribcage to expose the internal thoracic cavity, mediastinal space, and pericardium tissue PCT;

(f) incising the pericardium sac to expose at least a portion of the patient's beating heart containing the target coronary artery in need of a bypass graft;

(g) engaging tissue retraction means with a portion of the patient's incised pericardium tissue, as for example by piercing the pericardium tissue PCT with needle 11 of surgical suture 10 at point EP;

(h) applying tensile traction loads to the surgical suture 10 to position or orient the patient's beating heart through the retraction of pericardium tissue anatomically attached to said beating heart;

(i) to perform bypass grafts on the inferior or posterior coronary artery beds, preferably placing the beating heart in a verticalized position with the longitudinal axis of the heart assuming a substantially vertical orientation through the rotation of the apex of the heart relative to the base of the heart outwardly through the retracted ribcage;

(j) maintaining the pericardial retraction loads, and in part the position and orientation of the beating heart, by securing surgical suture 10 to a substantially stable surgical platform such as sternum retractor 5;

(k) securing surgical deflector tool 200 relative to the sternum retractor 5 at a location along one of the perimeter rails 70, 80, or 50 such that the subsequent deployment of said deflector tool 200 will result in the engagement of deflection member 210 with at least one surgical suture 10 and subsequently the deflection of said surgical suture 10;

(l) deploying the surgical deflector tool 200 by applying a manual push load to the proximal end 222 of arcuate connection member 220 resulting in an arcuate translation of said member 220 through housing 240 and a simultaneous movement of deflection member 210 which causes the deflection of surgical suture 10;

(m) within the enlarged surgical field created by the deflection of surgical sutures 10, deploying a coronary stabilizer to immobilize a portion of the beating heart in vicinity of Px;

(n) performing arteriotomy, anastomosis, and other surgical interventions on the target coronary artery;

(o) verifying the quality of the bypass graft by Doppler ultrasonography, or other like means, and redoing the bypass graft if not satisfied with the flow quality through the said bypass graft;

(p) disengaging the coronary stabilizer, or other like means, from the surface of the beating heart after the completion of the bypass graft;

(q) retrieving surgical deflector tool 200 from its deployed configuration to its non-deployed configuration;

(r) disengaging securing mechanism of surgical deflector tool 200, and retrieving said tool 200 from sternum retractor 5;

(s) disengaging tissue retraction means from pericardium tissue thereby removing the pericardial traction loads;

(t) delicately easing the beating heart back to into its substantially horizontal anatomic position within the retracted chest cavity;

(u) if desired, re-wrapping the incised pericardium tissue over patient's heart and securing said halves of incised pericardium to each other through the placement of surgical sutures;

(v) installing chest drainage tubes;

(w) closing retractor arms 3 and 4 and retrieving sternum retractor 5;

(x) closing the full or partial midline sternotomy incision.

The surgical procedure defined above, in broad terms also applies to the other embodiments of a surgical deflector tool according to the present invention, with the exception of specific references to the constituent components of surgical deflector tool 200.

Figure 7:
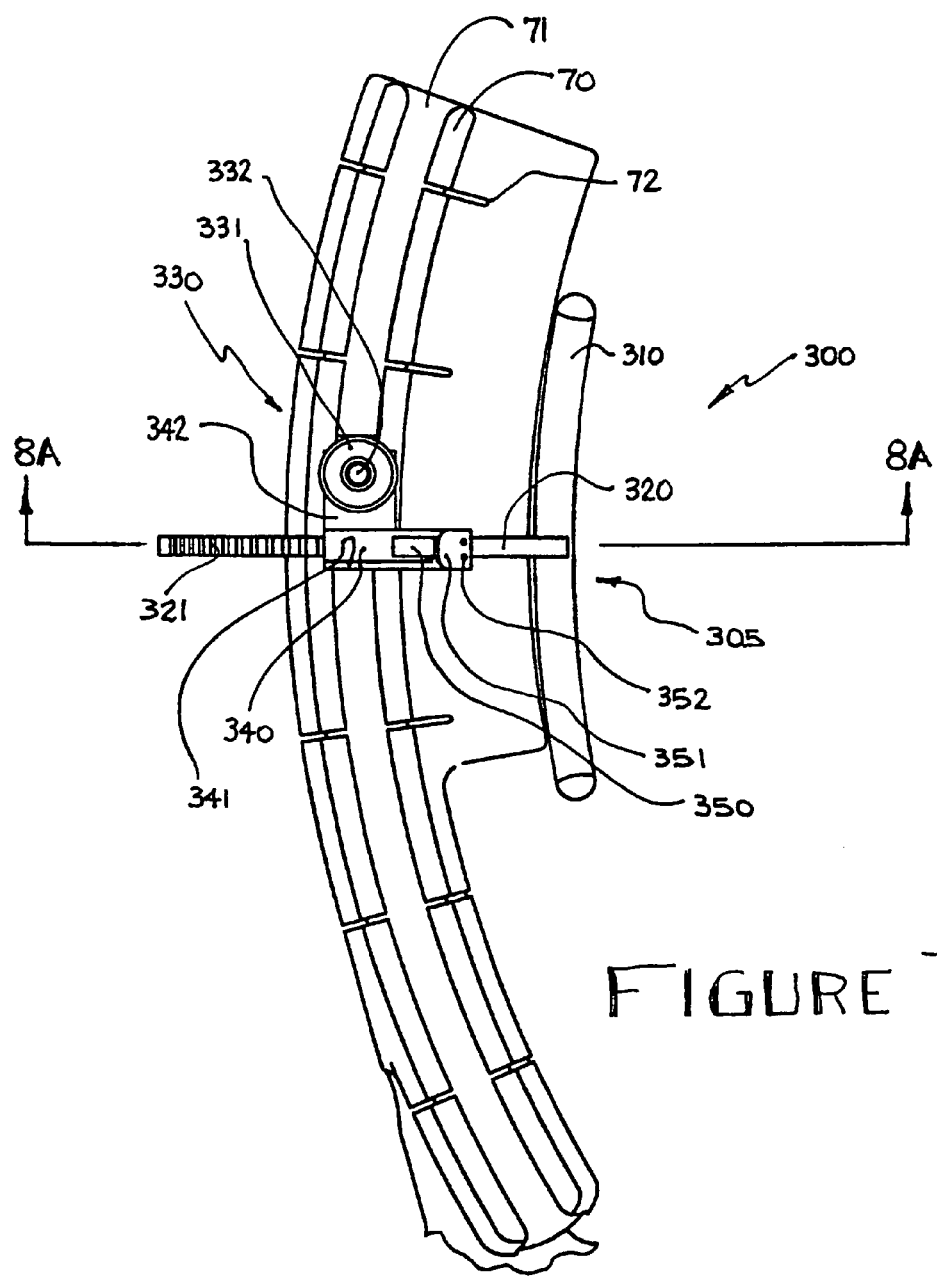
FIG. 7 is a top view illustrating a surgical deflector tool and a surgical apparatus with which the said surgical deflector tool may be used, according to a third embodiment of the present invention.
Figure 8A:
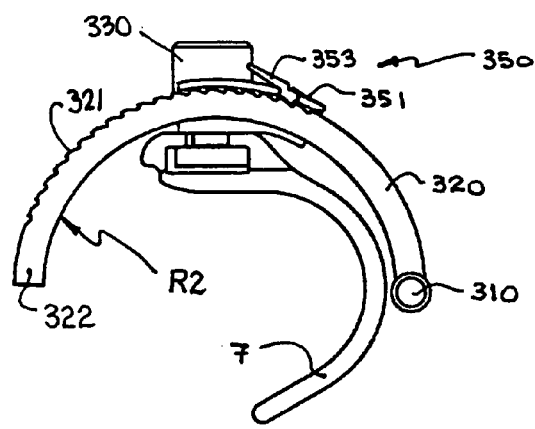
FIG. 8A is a section view through the surgical deflector tool illustrated in FIG. 7, illustrating said deflector tool in its non-deployed state.
Figure 8B:
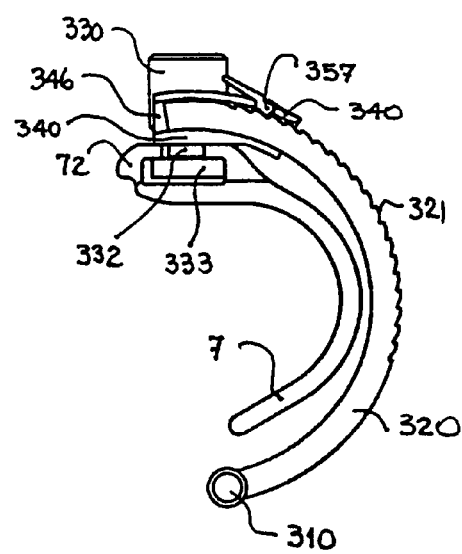
FIG. 8B is a section view through the surgical deflector tool illustrated in FIG. 7, illustrating said deflector tool in its deployed state.
Figure 11F:
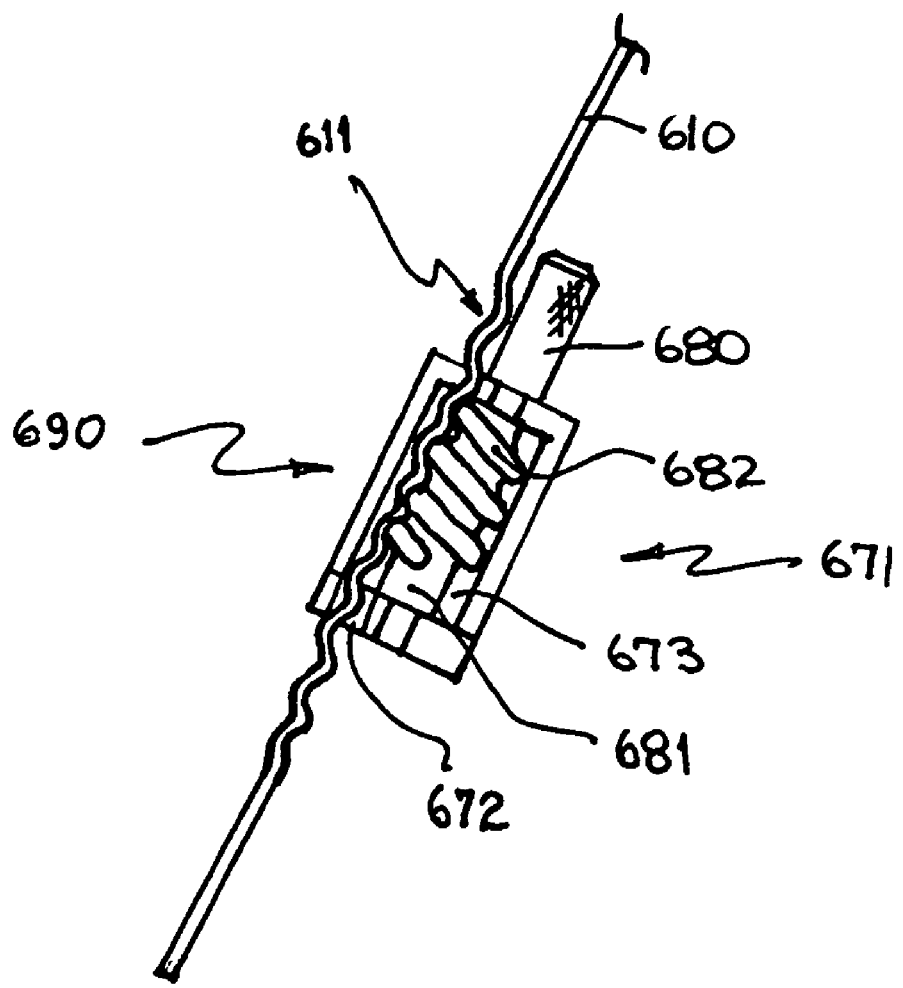
FIG. 11F is a section view through the surgical deflector tool illustrated in FIG. 11A, illustrating a housing and adjustment mechanism of said surgical deflector tool.

FIGS. 7, 8A and 8B illustrate a third embodiment according to the present invention. A surgical deflector tool 300 is comprised of a rod-like deflector 305, a securing mechanism in the nature of a threaded clamp 330, and an adjustment mechanism in the nature of a ratchet mechanism 350. Threaded clamp 330 is similar to threaded clamp 230 in the second embodiment.

Rod-like deflector 305 consists of a substantially arcuate elongate deflection member 310 and an arcuate connection member 320, preferably rigidly attached to said deflection member at its mid-span location. Rod-like deflector 305 is similar to rod-like deflector 205 except for outboard surface 221 of the second embodiment which is replaced by a toothed surface 321. Housing 340 is also similar to housing 240 of the second embodiment except for the provisions to receive an adjustment mechanism in the nature of a ratchet mechanism 350 instead of the wedge pin assembly 250 of the second embodiment. Ratchet mechanism 350 prevents the counterclockwise arcuate translation of connection member 320 through housing passage 346 unless the surgeon depresses lever 353 of pawl 357. Depressing lever 353 rotates pawl 357 out of engagement with the teeth on toothed surface 321 of connection member 320, thereby allowing the free arcuate translation of member 320 through housing 340. When deploying the surgical deflector tool 300, the surgeon applies a manual push load on the proximal end 322 of arcuate member 320. This manual push load causes the pawl 357 to rotate slightly as it disengages one tooth and engages the next tooth on toothed surface 321 of connection member 320. The counterclockwise rotation of pawl 357 is reacted in part by the spring preload imposed on it by spring element 351. Spring element 351 is attached to housing 340 through two mechanical fasteners or pins 352. Spring element 351 keeps the pawl 357 in contact with the toothed surface 321 and only allows clockwise arcuate translation of connection member 320 through housing 340 unless the action of the spring loaded pawl is manually overriden by depressing lever 353 at which point the connection member 320 is free to rotate in either a clockwise or counterclockwise arcuate translation.

FIGS. 9A–9C illustrate a fourth embodiment according to the present invention. A surgical deflector tool 400 is comprised of an arcuate elongate deflection member 410, a securing mechanism in the nature of two threaded clamps 430, a first connection member in the nature of a yoke support frame 420, and a second connection member in the nature of a pivot support frame 440. Threaded clamp 430 is similar to threaded clamp 230 in the second embodiment. Variations of threaded clamps which may apply this embodiment, or to some or all of the embodiments according to the present invention, are illustrated and described more fully below.

The two threaded clamps 430 are slidingly engaged within rails 80, 70 or 50 of sternum retractor 5. The two threaded clamps 430 are rotatingly engaged with their respective support frames 420 or 440. Once the desired position for the support frames 420 and 440 along the said rails is determined, the threaded clamps 430 are secured to the sternum retractor 5. The distance between both support frames 420 and 440 is variable depending on the surgical set-up and the number of tissue retraction means, for example surgical suture 10, to be engaged and deflected. Deflection member 410 is preferably formed in an arcuate shape of similar curvature to the arcuate spreader arms 3 and 4 when viewed from the top of the surgical window. The outboard surface 411 of member 410 is configured with a number of ridges or depressions which tend to improve adherence with tissue retraction means when said tissue retraction means is deflected by the deployment of surgical deflector tool 400. The ridges or depressions are preferably oriented such that their longitudinal axes are substantially parallel to the centerline defining arcuate curvature of member 410. Alternatively, outboard surface 411 may be configured with a texture to tend to improve adherence with said tissue retraction means.

Hole 441 in the proximal end of pivot support frame 440 rotatingly engages threaded clamp 430. The distal end of pivot support frame 440 pivotingly engages one end of deflection member 410. Threaded hole 444 in support frame 440 is engaged by a screw 414 after said screw 414 is inserted through hole 413 in member 410. Screw 414 acts as an axis of rotation, or pivot axis, for deflection member 410 when it pivots about the support frame 440. The other end of deflector member 410 is slidingly engaged in support frame yoke 427 configured at the distal end of support frame 420. A spring member 423 is housed in hole 424 in distal end of support frame 420, and energizes detent member 422. Detent member 422 will engage dimple 412 in deflection member 410 when said member 410 is inserted into yoke 427. The spring load exerted by detent member 422 on dimple 412 must be sufficient to keep deflection member 410 engaged within yoke 427 when the surgical deflector tool 400 is deployed and the deflecting load is applied to tissue retraction means. Alternatively, the detent member 422 may also be replaced by a pull-out pin or key, and dimple 412 replaced by a hole or keyway, respectively.

Support frame 440 is preferably configured with a generally arcuate shape in the vertical direction as illustrated in FIG. 9B, in order to clear the profile of blade 8 when support frame 440 is engaged with, and secured to, sternum retractor 5 through rail 80. Similarly, support frame 420 is preferably configured with a generally arcuate shape in the vertical direction as illustrated in FIG. 9C, in order to clear the profile of blade 7 when support frame 420 is engaged with, and secured to, sternum retractor 5 through rail 70. Surgical deflector tool 400 is illustrated in FIG. 9A with both support frames 420 and 440 engaged in rail 80 through threaded clamps 430. Alternatively, it may be deployed with both said support frames engaged in rail 70, or rail 50. Alternatively, it may be deployed with one said support frame engaged in a different rail than the other cooperating support frame. Pivot support frame 440 facilitates this since the deflection member 410 may assume a variety of angular orientations relative to pivot support frame 440 in order to engage yoke 427 of support frame 420 at its free end when both support frames are not on a common rail. The pivoting action of deflection member 410 may also allow it to engage a tissue retraction means and progressively deflect it as it pivots about screw 414 and finally comes to engage its free end with yoke 427.

As illustrated in FIG. 9A, deflection member 410 is engaged at each of its free ends with a connection member or support frame. As such, the engaged tissue retraction means lie, in use, between said connection members. Alternatively, the yoke support frame 420 may engage deflection member 410 in any one of its dimple 412 locations, for instance dimple location 415. As such, a portion of the deflection member 410 lies between the two said connection members, while a portion may lie cantilevered beyond the yoke support frame 420 but still able to deflect a surgical suture 10, if so engaged, over this said cantilevered portion.

FIGS. 10A–10C illustrate a fifth embodiment according to the present invention. A surgical deflector tool 500 is comprised of a louver-type deflector 510, a securing mechanisms in the nature of two threaded clamps 530, two support frames 520 and 540, and an adjustment mechanism in the nature of threaded member 590. Threaded clamp 530 is similar to threaded clamp 430 in the fourth embodiment. Support frames 520 and 540 engage sternum retractor 5 in a similar fashion and provide similar functionality as support frames 420 and 440 in the fourth embodiment except for differences at their distal ends where they engage louver-type deflector 510.

Louver-type deflector 510 is configured as a flat plate of thickness T and width W. A width W to thickness T ratio of approximately 4 to 7 is generally preferred. Two cylindrical extensions extend laterally beyond the length of louver 510 in opposing directions. One cylindrical extension is comprised of a shoulder 515 and a shaft member 516 which becomes rotatingly engaged with boss 521 on support frame 520. The other cylindrical extension is comprised of a shoulder 511, a shaft member 512 which becomes rotatingly engaged with boss 541 on support frame 540, and a thread 513 for engagement with threaded member 590. The centerline of both said cylindrical extensions are coincident to each other and define the pivot axis of louver-type deflector 510. This pivot axis is preferably offset a distance of 0.5 T–1 T in board from the width of said louvre-type deflector 510.

Boss 541 is pivotingly engaged to support frame 540 through pivot joint 549 (schematically represented as a trapped disc within a cylindrical bore arrangement) and similarly boss 521 is pivotingly engaged to support frame 520 through pivot joint 529. This allows the centerlines of hole 542 and centerline of hole 522 to pivot freely about their support frames 540, 520 and always become aligned relative to each other in order to engage shaft 512 and shaft 516 regardless of the position of support frames 520 and 540 along rail 80, 70, or 50, or any rail combination thereof. For instance, frame 540 may be engaged in rail 80 while cooperating frame 520 is engaged in rail 50, or frame 540 is engaged in rail 50 and frame 520 is engaged in rail 70, or with spreader arms 3, 4 sufficiently close together, frame 540 may be engaged in rail 70 and frame 520 is engaged in rail 80.

With reference to FIG. 10B, the louver-type deflector 510 is illustrated in its non-deployed configuration or state (drawn in solid line) and a deployed configuration or state (drawn in dashed line). In its non-deployed configuration, deflector 510 is in slight contact with surgical suture 10 which assumes an initial non-deflected vector direction V1 when engaged simultaneously with PCT and sternum retractor 5. In a deployed configuration, deflector 510 is engaged with surgical suture 10 which assumes its deflected vector direction V2.

After the pericardial traction sutures 10 have been secured to the sternum retractor in a manner as described above, the surgical deflector tool 500 is engaged and secured in place along rail 80, for example, through threaded clamps 530. At this point, louver-type deflector 510 is in its non-deployed configuration or state. To achieve the deflection of surgical suture 10, from a vector V1 to vector V2 orientation, louver-type deflector 510 is rotated by the surgeon (clockwise with reference to FIG. 10B) until the desired surgical suture 10 deflection is achieved. At this point, threaded member 590 is tightened thereby clamping the lateral faces of boss 541 between shoulder 511 and lateral face of threaded member 590. This secures the louver-type deflector in a desired angular orientation about its pivot axis. In-process readjustments may be made by the surgeon by loosening threaded member 590, readjusting the angular orientation of louver-type deflector 510 about its pivot axis, and re-tightening said threaded member 590. As such, deflector 510 may be set in a continuously variable range of angular orientations. Alternatively, other types of adjustment mechanisms may be used in place of threaded member 590.

For instance, a ratchet mechanism consisting of a pawl housed in boss 541 that engages with teeth added to outer surface of shaft 512 may also be used, or other like adjustment mechanisms.

FIGS. 11A–11F illustrate a sixth embodiment according to the present invention. A surgical deflector tool 600 is comprised of a deflection member in the nature of a continuous strip or band-type deflector 610, a securing mechanisms in the nature of a plurality of threaded clamps 630 (four illustrated), a plurality of connection members or support frames 640, 650, 660, 670, and an adjustment mechanism in the nature of a worm-gear assembly 690. Threaded clamp 630 is similar to threaded clamp 430 in the fourth embodiment. Support frames 640, 650, 660, and 670 engage sternum retractor 5 in a similar fashion as support frames 420 or 440 in the fourth embodiment.

Continuous band-type deflector 610 is intended to simultaneously engage and deflect all surgical sutures 10 that may be deployed and secured around the perimeter of sternum retractor 5. Deflector 610 is rigidly engaged to flange 641 of support frame 640 by either a welded joint or a mechanically fastened joint or other like means. Deflector 610 is preferably a sheet metal strip configured with a rectangular cross-section. The thickness of said deflector is considerably narrower than its cross-sectional height. This provides flexibility along the length of the deflector and substantial rigidity along the height of the deflector.

The band-type deflector 610 is free to slide through rectangular opening 652 in flange 651 of support frame 650, free to slide through rectangular opening 662 in flange 661 of support frame 660.

Support frame 670 is configured with a housing 671 that contains worm-gear assembly 690 rotatingly engaged within cylindrical opening 673. Band-type deflector 610 is not free to slide through rectangular opening 672 of housing 671, but may translate through said rectangular opening 672 by virtue of a rotation of knob 680 which rotates helical worm 682 thereby entraining serrations 611 and the said translation of deflector 610.

Each support frame has a substantially flexible portion 649, 659, 669, and 679 along its arcuate vertical length. With the threaded clamps 630 securing the position of their respective support frames 640, 650, 660, and 670 on the rails 80, 70, and 50 of sternum retractor 5, rotating knob 680 in one direction causes the length of band-type deflector 610 between flange 641 and housing 671 to increase. The flexible portions 649, 659, 669, and 679 will consequently flex in a direction laterally away from the patient's beating heart (or the center of the retracted chest opening), thereby also tending to increase the amount of deflection simultaneously exerted on the plurality of surgical sutures 10 that may be deployed and secured along the perimeter of sternum retractor 5. During the flexing of support frames 650 and 660, the deflector 610 slides through the openings 652 and 662 of said support frames 650 and 660.

FIGS. 12–17 illustrate a variety of different securing mechanism. FIGS. 12A–12B illustrate a securing mechanism in the nature of a T-nut assembly 710 comprising T-nut 712 and co-operating bolt 711. In this embodiment, the T-nut 712 is installed into arcuate passage 81 (or 71 or 51). Then, contact surface 113 of baffle 110 is brought into contact with one or more tissue retraction means. The tissue retraction means is deflected until a hole in said baffle is aligned with threaded hole in T-nut 712. Bolt 711 is then engaged with co-operating T-nut 712 and baffle secured in place by the resulting clamping force between the said T-nut 712 and bolt 711. Baffle 110 may also be configured with more than one hole in its connection member 112 to provide variability in the secured position of the deflecting contact portion 113 relative to the said sternum retractor.

Figure 13A:
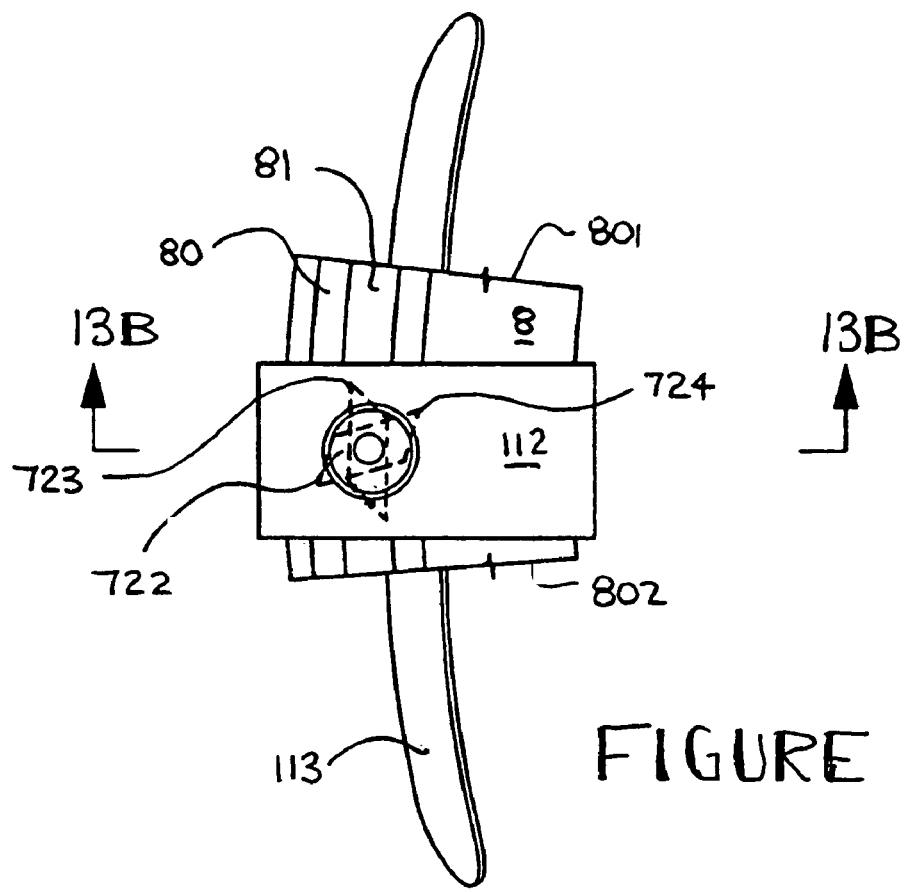
FIG. 13A is a top view illustrating a variant securing mechanism in the nature of a modified T-bolt, according to the present invention.
Figure 13B:
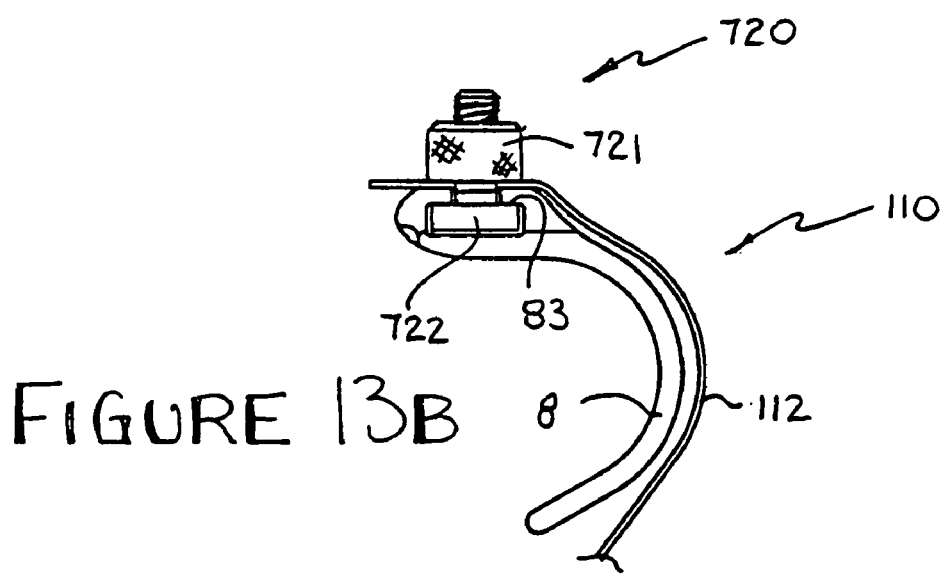
FIG. 13B is a section view through the variant securing mechanism illustrated in FIG. 13A.

FIGS. 13A–13B illustrate a securing mechanism in the nature of a modified T-bolt assembly 720 comprising T-bolt 722 and co-operating nut 721. The parallelogram shape of the modified T-bolt 722 allows the deflector baffle 110 to become engaged with and secured relative to rail 80 (or 70 or 50) through a clockwise rotation of nut 721 without having to first slide bolt 722 into arcuate passage 81 (or 71 or 51). When bolt 722 is aligned lengthwise with arcuate rail 80 (orientation 723), it may be inserted into arcuate passage 81. A clockwise rotation of nut 721 will cause bolt 722 to rotate clockwise up until its short faces are in substantial contact with the lateral faces of arcuate passage 81 (orientation 724). As a result, a portion of parallelogram shaped top face of T-bolt 722 comes into contact with faces 83 of rail 80. A further rotation of nut 721 will clamp deflector baffle 110 between nut 721 and top of rail 80.

Figure 14B:
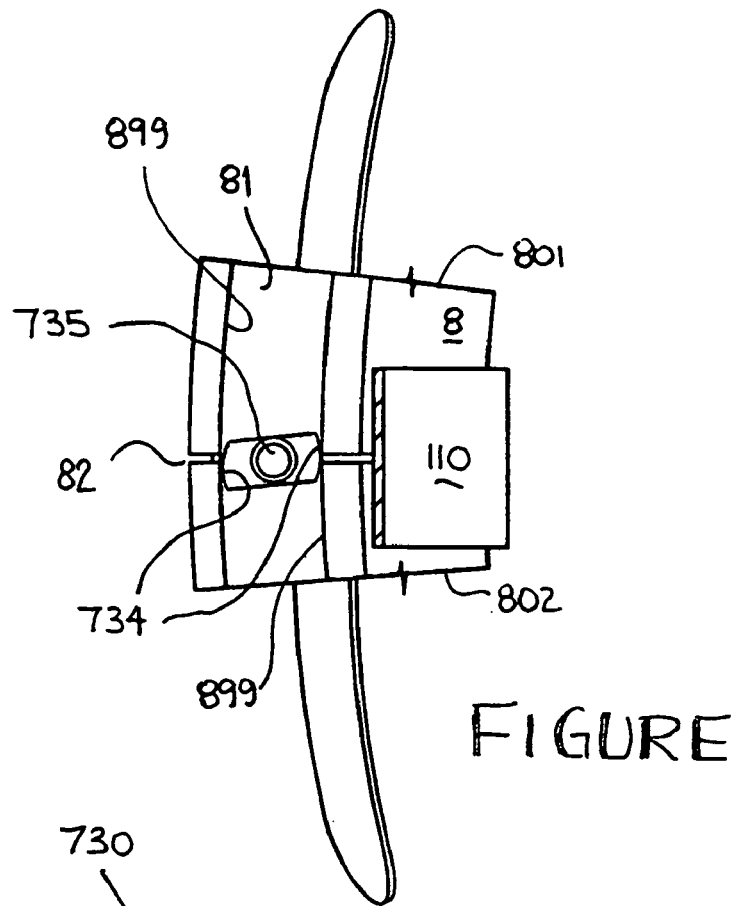
FIG. 14B is a section view through the variant securing mechanism illustrated in FIG. 14A.
Figure 14A:
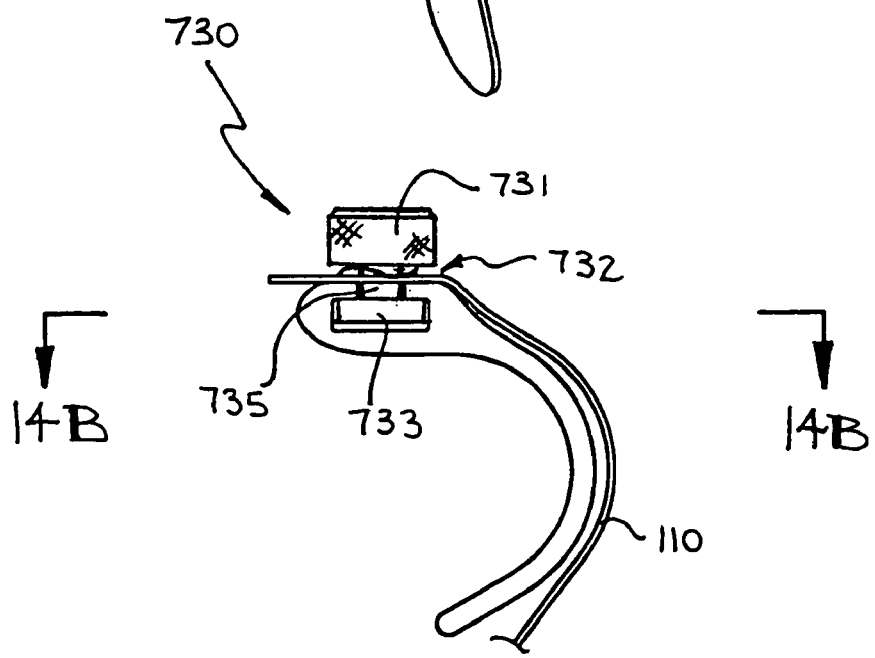
FIG. 14A is a side elevational view illustrating a variant securing mechanism in the nature of a radially-engaging cam, according to the present invention.

FIGS. 14A–14B illustrate a securing mechanism in the nature of a radial engaging cam 730 comprising a radial engaging cam 733, a shaft 735, a wave spring washer 732 and a securing knob 731. Radial engaging cam 730 is rotatingly engaged with deflector baffle 110 to form an intergral mechanical assembly. The deflector baffle 110 is secured relative to sternum retractor 5 within arcuate passage 81 when knob 731 is rotated thereby radially engaging the two opposing cam surfaces 734 with the lateral walls 899 defining arcuate passage 81 (or 71 or 51). The clamping load on baffle 110 is provided by compressing wave spring 732.

Figure 15B:
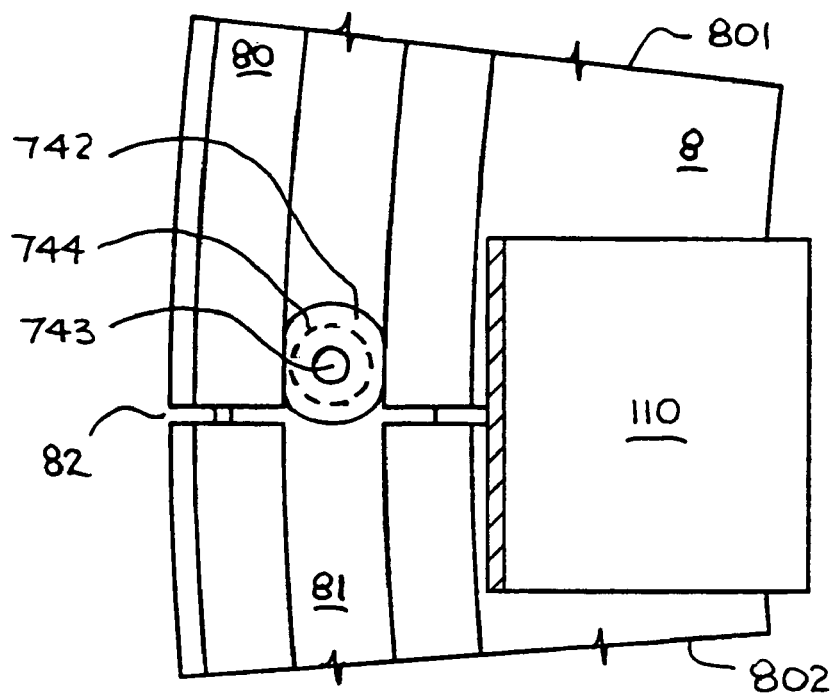
FIG. 15B is a section view through the variant securing mechanism illustrated in FIG. 15A.
Figure 15A:
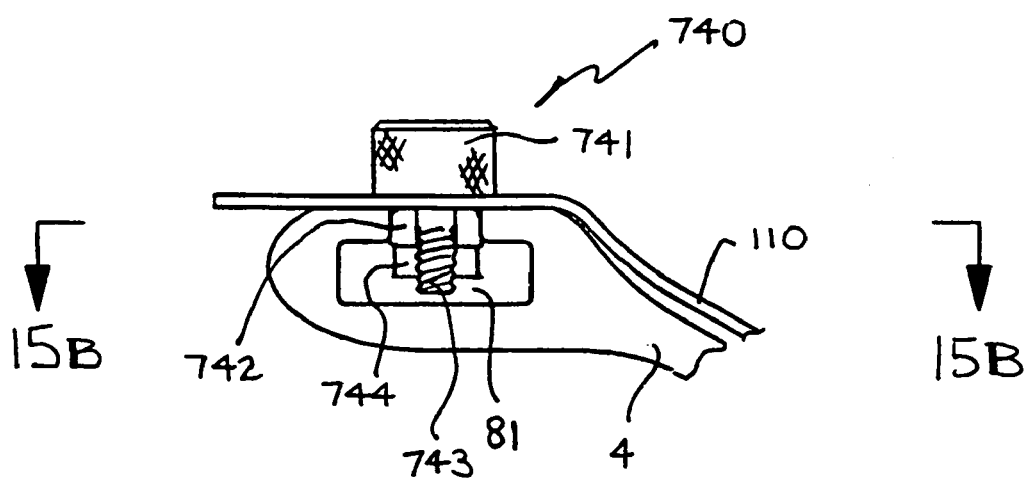
FIG. 15A is a side elevational view illustrating a variant securing mechanism in the nature of a grommet-type expansion joint, according to the present invention.

FIGS. 15A–15B illustrate a securing mechanism in the nature of a grommet-type expansion joint 740 comprising a bolt 741, an elastic annular washer 742, and a clamping plate 744. Prior to installation, clamping plate 744 is in substantial contact with elastic washer 742. Once the grommet-type expansion joint 740 is inserted into arcuate rail 80 (or 70 or 50) a rotation of bolt 741 produces an axial compression of washer 742 and a simultaneous radial expansion of washer 742. This radial expansion produces the engagement between washer 742 and the lateral walls of arcuate passage 81 (or 71 or 51). The friction between clamping plate 744 and elastic washer 742 keeps said plate 744 from rotating relative to said washer 742 when knob 741 is tightened.

Figure 16:
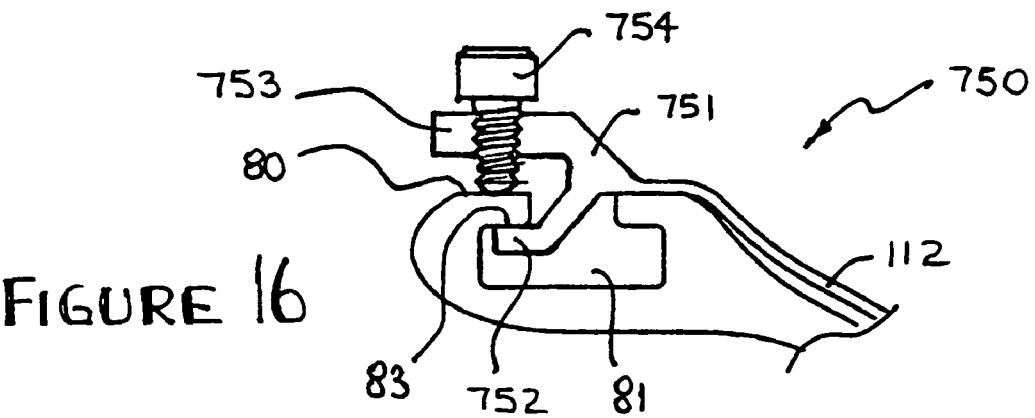
FIG. 16 is a side elevational view illustrating a variant securing mechanism in the nature of a C-shape flange, according to the present invention.

FIG. 16 illustrates a securing mechanism in the nature of a C-shaped flange 750 comprising a bolt 754, two extensions 753 and 752, and a joining section 751. Deflector connection member 112 is engaged with rail 80 of sternum retractor 5 through a clockwise rotating motion that brings into contact extension 752 with underside surface 83 in arcuate passage 81. Bolt 754 is subsequently tightened to prevent a reverse counterclockwise rotating motion and disengagement of said connection member and consequently the surgical deflector tool.

Figure 17:
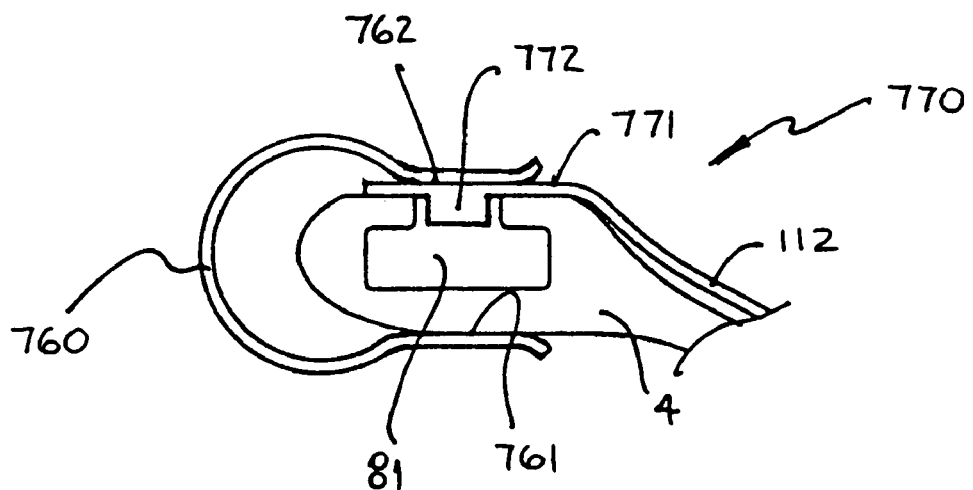
FIG. 17 is a side elevational view illustrating a variant securing mechanism in the nature of a retaining clip, according to the present invention.

FIG. 17 illustrates a securing mechanism in the nature of a retention clip 760. Deflector baffle 770 is inserted into arcuate passage 81 (or 71 or 51) through the engagement of anti-rotation block 772 extending from flat surface 771. Retention clip 760 is then installed such that its surfaces 761 and 762 simultaneously contact the bottom surface of retractor arm 4 and the top surface 771 of baffle 770.

Figure 18A:
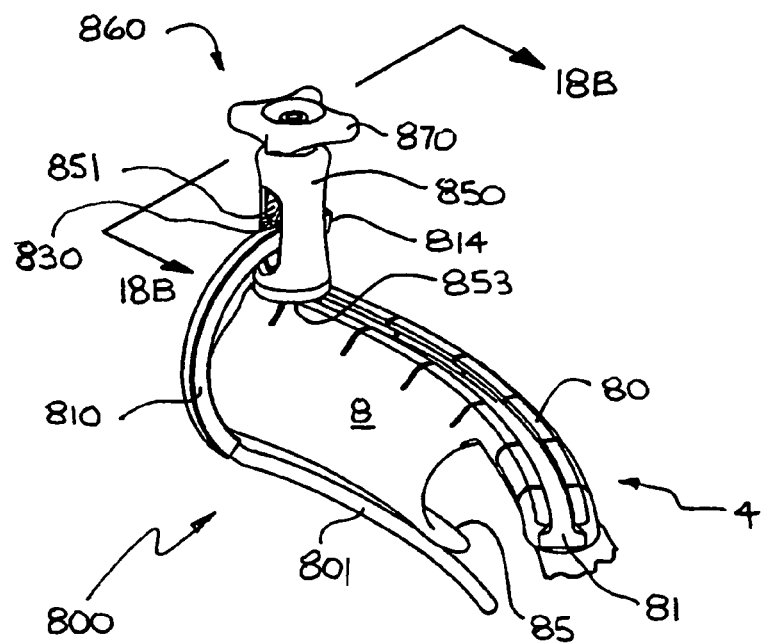
FIG. 18A is a perspective view illustrating a surgical deflector tool and a surgical apparatus with which the said surgical deflector tool may be used, according to a seventh embodiment of the present invention.
Figure 18B:
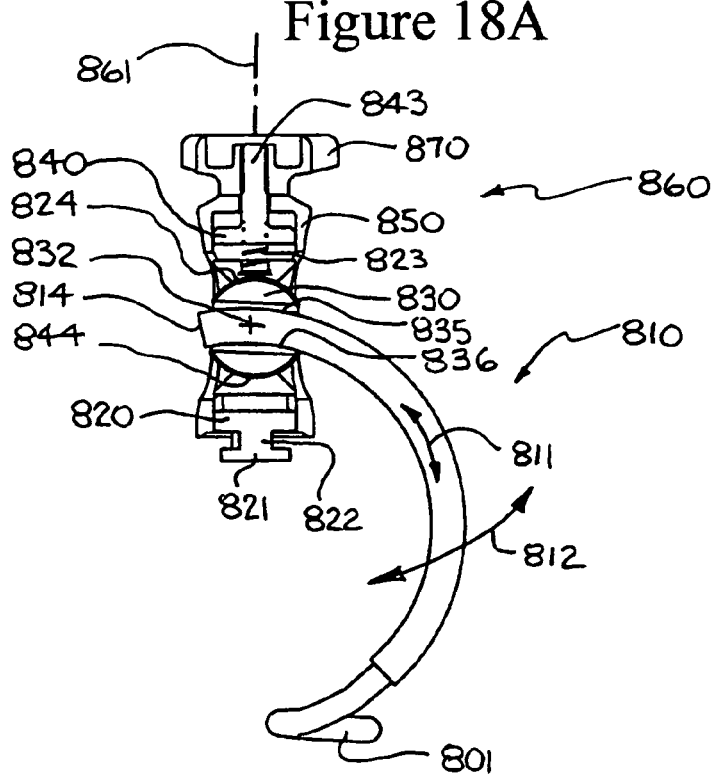
FIG. 18B is a section view through the surgical deflector tool illustrated in FIG. 18A, illustrating said deflector tool in its deployed state.
Figure 18C:
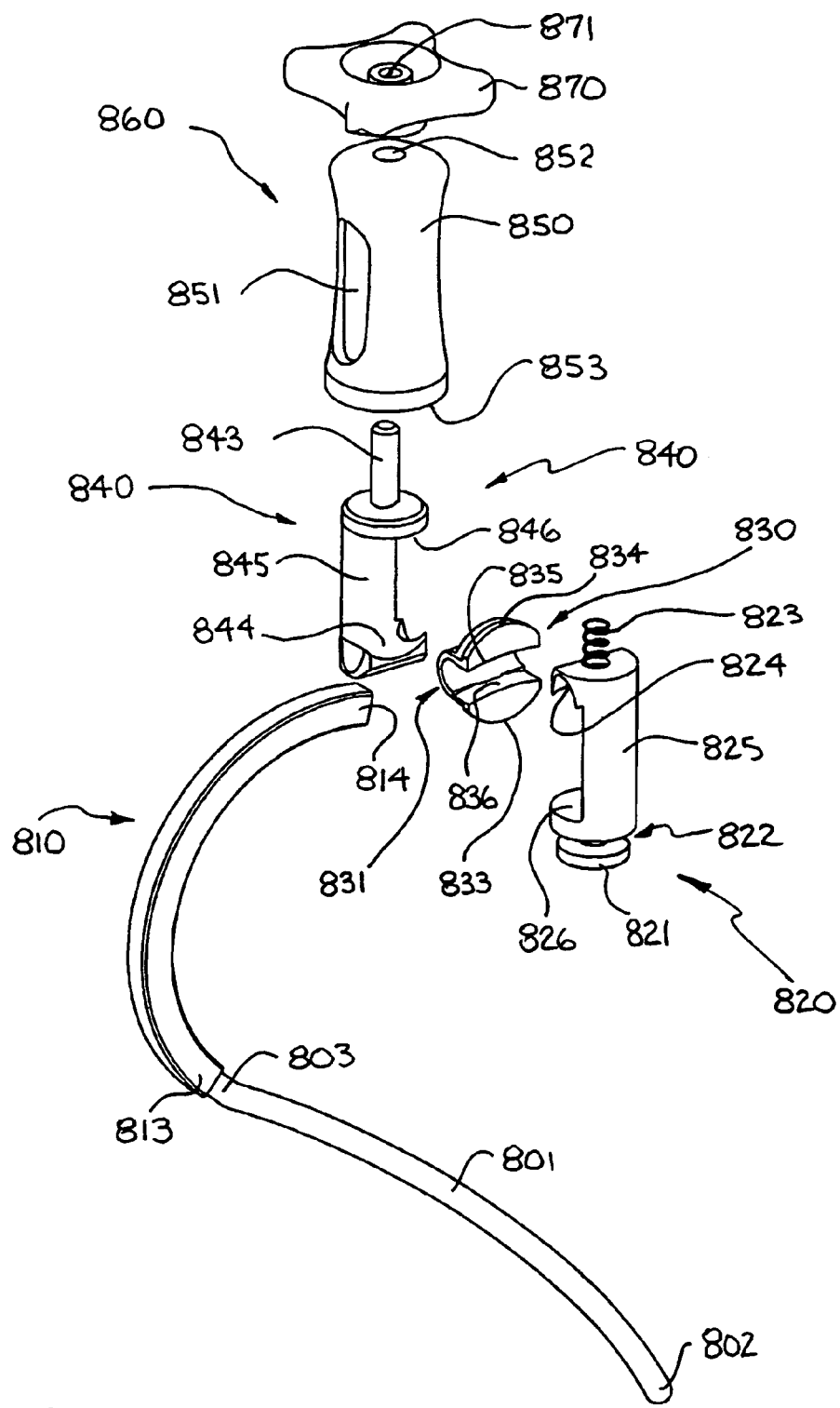
FIG. 18C is an exploded view of the surgical deflector tool illustrated in FIG. 18A.

FIGS. 18A–18C illustrate a seventh embodiment according to the present invention. Surgical deflector tool 800 is comprised of an elongate rod-like deflection member 801, an arcuate connection member 810 and a securing mechanism 860. Deflection member 801 is preferably configured with an arcuate shape similar in shape to that of the arcuate shape of retractor spreader arm 4. Deflection member 801 is comprised of a free end 802 and a joined end 803 that is preferably rigidly connected to distal joined end 813 of connection member 810, such as through a press fit interface, a weldment, a brazed joint, a mechanical fastener joint, or any other like rigid connection joint. As such, when joined, connection member 810 and deflection member 801 form an integral assembly that is substantially L-shaped (as opposed to the second embodiment where said deflection and connection members form an integral assembly that is substantially inverted T-shaped). For ease of manufacturing, connection member 810 is preferably an arcuate sector of a metal ring or metal annulus. The cross-section through connection member 810, generated by a cut normal to the arcuate shape, is rectangular in shape.

Securing mechanism 860 forms a demountable mechanical assembly and is comprised of a slotted articulation cylinder 830, two opposing co-operating jaws 820, 840, a housing sleeve 850, and a securing knob 870. A longitudinal axis 861 helps define the securing mechanism 860 and its components, along with the longitudinal direction through said components.

Articulation cylinder 830 is defined by a centerline axis 832 (seen in end view in FIG. 18B). A transverse arcuate slot 831 is disposed substantially along a diameter of said cylinder. As such, two opposing cylindrical contact surfaces 833, 834 and two opposing arcuate internal contact surfaces 835, 836 are created. In use, slot 831 will engage a portion of connection member 810. A mechanical load applied across contact surfaces 833, 834 will deform slot 831 in a manner that a compressive force will be transmitted to the engaged portion of connection member 810 within slot 831 through arcuate contact surfaces 835, 836.

Jaws 820, 840 are substantially cylindrical in shape along their longitudinal axes. A longitudinal slot is contained within said cylindrical shape to create two opposing C-shaped jaws. The C-shape in each of said jaws is defined by a face 826 or 846, a beam 825 or 845, and a socket 824 or 844. Sockets 824, 844 are defined by substantially cylindrical contact surfaces. Lower jaw 820 is configured with a spring member 823 that is energized when a mechanical load is applied generally along the longitudinal axis of said jaw 820. When said jaws 820, 840 are assembled, spring member 823 of jaw 820 mates with face 846 of jaw 840 and entrains opposing sockets 824, 844 to move towards one another in a longitudinal direction. A central opening is created between assembled jaws 820, 840 able to receive articulation cylinder 830. Said opening is defined laterally by opposing beams 825, 845 and longitudinally by opposing sockets 824, 844. Sleeve 850 is inserted over assembled jaws 820, 840 in a manner that external thread 843 is inserted through hole 852 and extends beyond top of said sleeve. As such, said thread 843 may be engaged with internal thread 871 in knob 870.

Sleeve 850 is configured with two diametrically-opposite, longitudinally-elongate windows 851. Sleeve 850 may be rotated such that said windows 851 become aligned with said central opening created within assembled jaws 820, 840. Windows 851 are at least as wide as lateral width defined between beam portions 825, 845 of assembled opposing jaws 820, 840. Said lateral width is preferably only slightly wider than width of articulation cylinder 830. As such, articulation cylinder 830 may be inserted through one of said windows with its centerline axis 832 oriented substantially perpendicular to longitudinal axis 861. After insertion, contact surface 834 is in contact with socket 824, and contact surface 833 is in contact with opposing socket 844. As such, cylinder 830 and jaws 820, 840 co-operate to allow contact surfaces 833, 834 to rotate freely between sockets 824, 844 when knob 870 is not tightened. The proximal free end 814 of connection member 810 can be inserted into slot 831 when said slot is visible through window 851.

Lower jaw 820 is configured with a seat 821 and waist diameter 822 that extend below base 853 of sleeve 850 when securing mechanism is assembled. Seat 821 and waist diameter 822 thereby allow securing mechanism 860 (and consequently deflector tool 800) to be slidingly engaged with any of passages 81, 71, or 51 and positioned at any location along along rails 80, 70, or 50 of sternum retractor 5. At any such given position along said rails, waist diameter 822 also allows securing mechanism 860 (and consequently deflector tool 800) to rotate freely about its longitudinal axis 861, prior to tightening knob 870.

Alternatively, lower jaw 820 may be configured with an anti-rotation feature at location of waist diameter 822, for instance two substantially parallel and opposing flats spaced apart a distance slightly inferior to the lateral width of passage 81, 71, or 51. Said flats will mate with lateral faces of said passage to restrict or prevent the free rotation of securing mechanism 860 (and of deflector tool 800) relative to sternum retractor 5. Said flats, however, allow the free translation of securing mechanism 860 along said rail 80, 70, or 50 when knob 870 is not tightened.

When engaged along a rail 80, 70, or 50 of sternum retractor 5, longitudinal axis 861 of securing mechanism is substantially perpendicular to the top of said retractor rail in which securing mechanism 860 is engaged.

In use, connection member 810 is slidingly engaged with articulation cylinder 830, and when securing knob 870 is not tightened, said member 810 is free to arcuately translate through said cylinder 830. This said arcuate translation is represented schematically in FIG. 18B as arrow 811. Any portion of connection member 810 may be engaged within slot 831, thereby providing a continuous range of arcuate settings (between proximal free end 814 and joined distal end 813) that connection member 810 may assume relative to securing mechanism 860. This also sets the general position of deflection member 801 relative to the sternum retractor 5, and also relative to the engaged anatomic tissue intended to be deflected.

In use, when securing knob 870 is not tightened, articulation cylinder 830 is free to rotate about its centerline 832 within the assembled securing mechanism 860. As such, when connection member 810 is engaged within slot 831 of cylinder 830, connection member 810 is also pivotingly engaged with respect to securing mechanism 860 and able to pivot about centerline 832 as cylinder 830 rotates within co-operating, opposed jaws 820, 840. A continuous range of pivot or angular settings is offered. This said pivoting of connection member 810 is represented schematically in FIG. 18B as arrow 812. Said range of angular settings is generally limited by the longitudinal width of window 851, or by the circumferential gap between assembled sockets 824 and 844. As a result, at any given arcuate setting of connection member 810 relative to securing mechanism 860, said member 810 may be further set or additionally adjusted in a desired angular setting relative to securing mechanism 860. The available range of angular settings allows the surgeon to set the general orientation of connection member 810 and deflection member 801 relative to sternum retractor 5, and also relative to the engaged anatomic tissue intended to be deflected.

When deflector tool 800 is in its non-deployed configuration, distal joined end 813 of connection member 810 is in the vicinity of window 851, and deflection member 801 is in the vicinity of engaged rail 80, 70, or 50. In use, when deflector tool 800 is in its deployed configuration, proximal free end 814 of connection member 810 is in the vicinity of window 851, and deflection member 801 is in the vicinity of free end 85 of blade 8, or 7. To deploy said tool 800, the surgeon applies a manual load to free end 814 to produce an arcuate translation and achieve a desired arcuate setting, or applies a moment (about centerline 832) to connection member 810 to orient said connection member and set the desired angular setting, or applies a combination of said manual load and said moment. In deploying deflector tool 800, the surgeon first brings into contact deflection member 801 with at least one tissue retraction means and subsequently deflects said retraction means or anatomic tissue in a manner already described according to the present invention.

When knob 870 tightened, the two opposing jaws 820, 840 co-operate to clamp articulation cylinder 830 across its opposing contact surfaces 834, 833. A compressive load is applied to the portion of connection member 810 engaged within slot 831 of said cylinder 830. As a result, (i) the arcuate translation of connection member 810 through securing mechanism 860 is locked and said connection member 810 is no longer slidingly free, (ii) the rotation of cylinder 830, and pivoting of connection member 810 about securing mechanism 860, is locked or fixed, and (iii) the location of deflector tool 800 along engaged rail 80, 70, or 50 is locked or fixed.

Securing mechanism 860 allows in-process readjustments to the surgical set-up of deflector tool 800. Loosening knob 870 will allow the surgeon to reposition securing mechanism 860 along engaged rail 80, 70, or 50, or reposition connection member 810 through articulation cylinder 830, or reorient said connection member relative to securing mechanism 860, without disengaging deflector tool 800 from sternum retractor 5.

Figure 19:
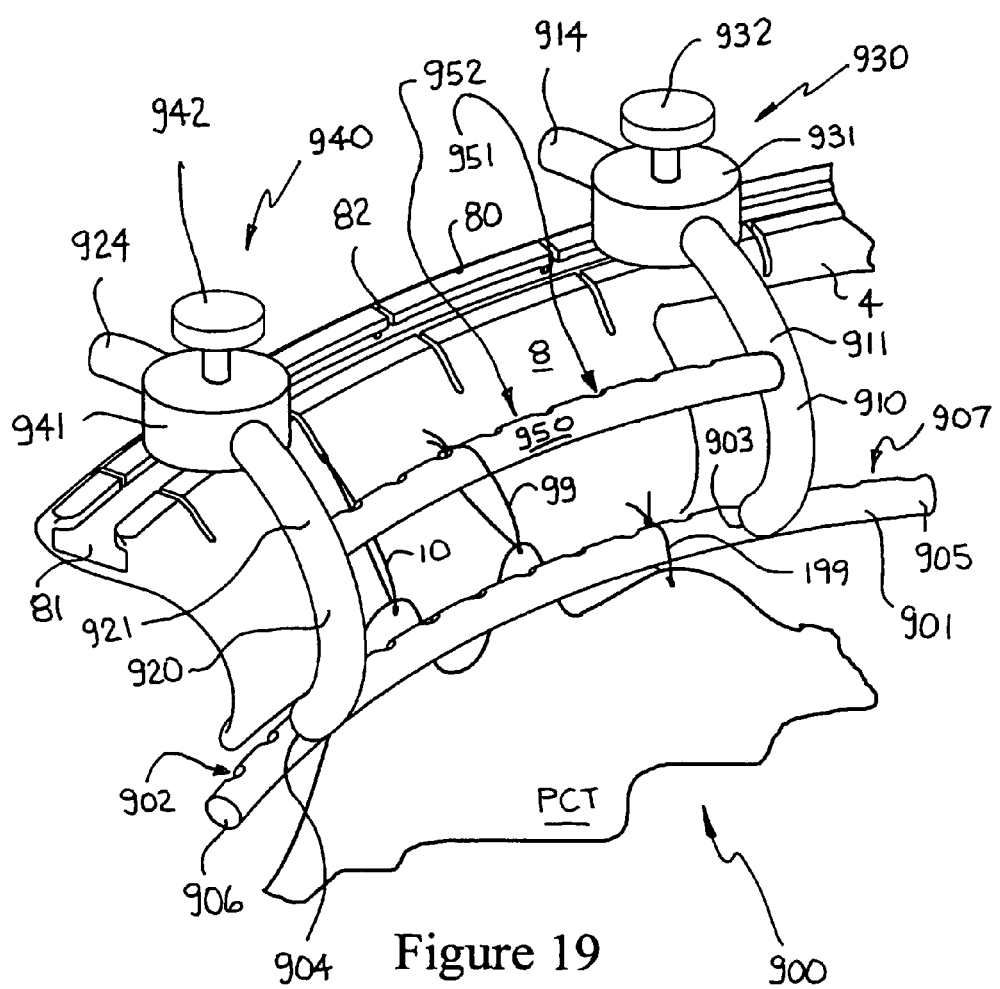
FIG. 19 is a perspective view illustrating a surgical deflector tool and a surgical apparatus with which the said surgical deflector tool may be used, according to an eight embodiment of the present invention.

FIG. 19 illustrates an eighth embodiment according to the present invention. Surgical deflector tool 900 is comprised of an elongate rod-like deflection member 901, two arcuate connection members 910, 920, and two securing mechanisms 930, 940. Deflection member 901 is preferably configured with an arcuate shape and is preferably rigidly connected to each of connection members 910 and 920. As such, when joined, connection members 910, 920 and deflection member 901 form an integral assembly that is substantially U-shaped.

Securing mechanisms 930, 940 are schematically represented by a housing 931, 941 and a securing member 932, 942. In this eight embodiment, connection member 910, 920 are rigidly connected to housing 931, 941 of securing mechanisms 930, 940 (even when securing members 932, 942 are not actuated). As such, securing mechanisms 930, 940 are comprised of similar components as those described, for instance, in the variants illustrated in FIGS. 13, 14, 15. When securing members 932, 942 are not actuated, deflector tool 900 is free to slide along engaged rail 80, 70, or 50 of sternum retractor 5.

Prior to deploying deflector tool 900, the pericardium tissue PCT is first engaged by a tissue retraction means such as surgical suture 10, said suture is then inserted in slit-like channel 82, and subsequently secured to a part of the sternum retractor 5. Said suture is usually secured under tension and preferably applies at least a slight retraction load on engaged PCT. The deflector tool 900 is then deployed in a manner that deflection member 901 is brought into contact with and subsequently deflects at least one surgical suture 10 or a portion of retracted pericardium tissue PCT. The imposed deflection on surgical suture 10 or pericardium tissue PCT is maintained by engaging securing mechanisms 930, 940 in rail 80 (or 70, or 50) and actuating their respective securing members 932, 942. The position of deflector tool 900 along rail 80 (or 70, or 50) may be readjusted by releasing securing members 932, 942 and sliding said tool 900 along said rail. Deflection member 901 is comprised of a deflector portion which spans between connection points 903, 904, but may also span beyond said connection points to reach free end points 905, 906. Deflection member 901 is preferably configured with a plurality of traction channels, slots, or grooves 902 along its contact surface 907. Said traction grooves 902 may help to engage and laterally restrain a tissue retraction means as it is being deflected, or help promote adherence with pericardium tissue PCT when said tissue is in contact with contact surface 907 and being deflected by said deflection member 901.

Alternatively, a variant deflector tool 900 may be comprised of two securing mechanisms that permit the translation of connection members 910, 920 through said securing mechanisms, or permit translation and pivoting of said connection members relative to said securing mechanisms. For example, these types of securing mechanisms may be comprised of similar components as those described in the embodiments illustrated in FIGS. 4, 7, 18, or any other suitable securing mechanism described herein. In addition, this variant may be comprised of a tying member 950 preferably connected to both connection members 910, 920. When this variant is in its non-deployed configuration, said tying member 950 is in the vicinity of rail 80 (points 911, 912 are located in the vicinity of securing mechanisms). As such, this offers a different method for securing tissue retraction means. In certain surgeries it may be advantageous to engage an anatomic tissue intended to be deflected with a tissue retraction means, such as surgical suture 99, and subsequently securing said surgical suture 99 to a portion of the deflector tool prior to its deployment. For instance, prior to said deployment, surgical suture 99 may be secured to tying member 950, preferably while said suture is under tension and applies a retraction load to said anatomic tissue. The deflector tool is subsequently deployed by applying a manual load on proximal free ends 914, 924 of connection members 910, 920 which results in tying member 950 moving away from rail 80 within retracted chest cavity, and deflection member 901 deflecting suture 99 or portion of pericardium tissue PCT engaged by said suture 99. Alternatively, while this variant is in its non-deployed configuration, pericardium tissue PCT may also be engaged, retracted, and secured to deflection member 901 by a surgical suture 199. Tying member 950 is configured with a plurality of traction grooves 951 along its contact surface 952 which serve the same role as traction grooves 902 on deflection member 901.

Figure 20:
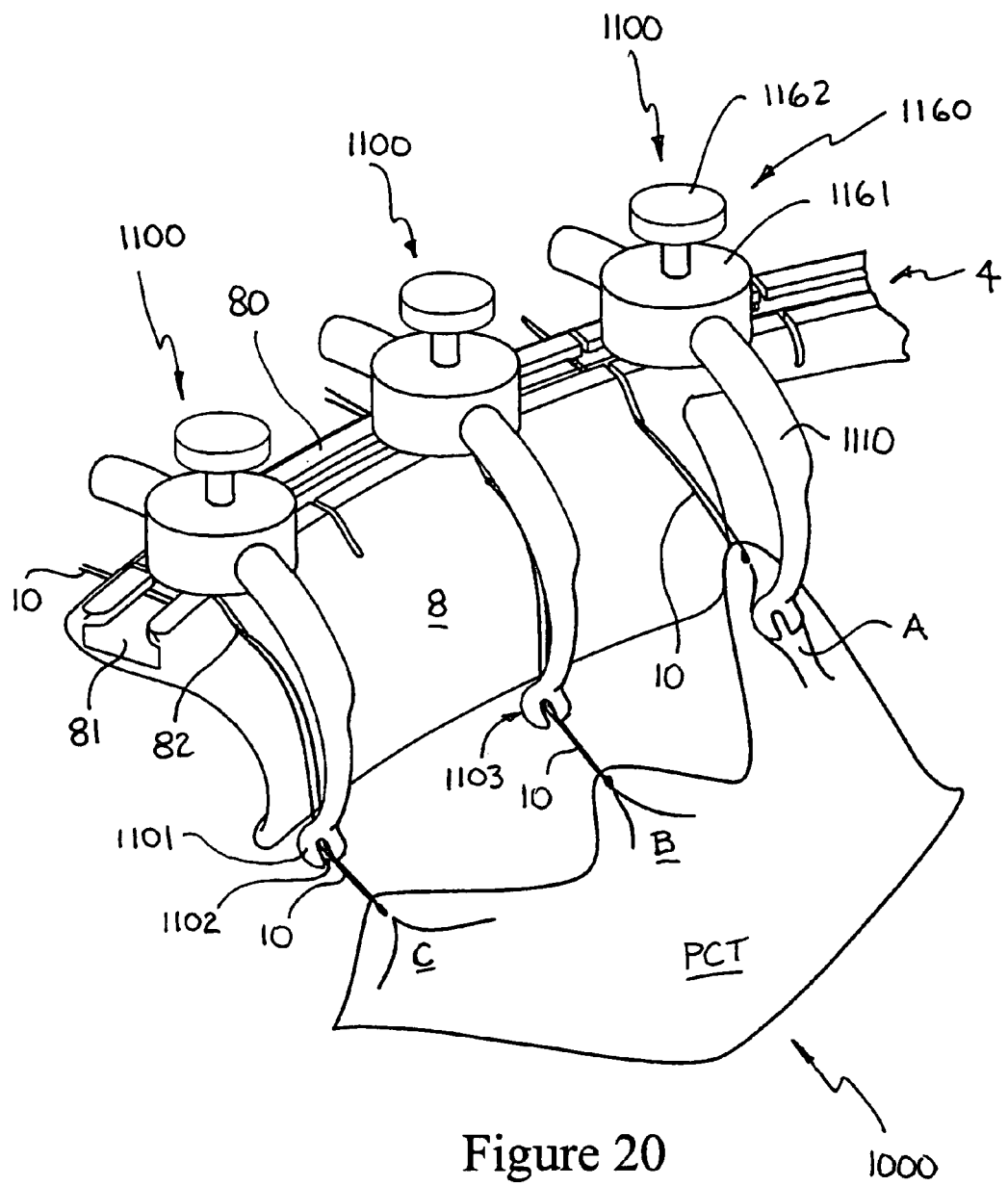
FIG. 20 is a perspective view illustrating a surgical deflector arrangement and a surgical apparatus with which the said surgical deflector arrangement may be used, according to an ninth embodiment of the present invention.

FIG. 20 illustrates a ninth embodiment according to the present invention. Surgical deflector arrangement 1000 is comprised of a plurality of surgical deflector tools 1100. Each of said surgical deflector tools 1100 is further comprised of deflection pad 1101, a connection member 1110, and a securing mechanism 1160. Each of the deflector tools 1100 may be independently positioned and secured along either one of rails 80, 70, or 50, and is preferably slidingly engaged with said rails.

Deflection pad 1101 is preferably configured with a slot 1102 that is well suited to laterally engage a tissue retraction means, such as suture 10, during intended deflection of said suture. Deflection pad 1101 may either engage and deflect a surgical suture 10 (as in location B and C), or may engage and deflect a portion of pericardium tissue PCT, preferably in the vicinity of where said portion of PCT is being retracted and engaged by a suture 10 (as in position A). As such, deflection pad contact face 1103 is preferably configured with friction-enhancing surface texture like surface texture 118 described with reference to FIG. 12A.

Connection means 1110 is preferably arcuate in shape. Securing mechanism 1160 is schematically represented by a housing 1161 and a securing member 1162. Securing mechanism 1110 may represent any suitable securing mechanism previously described in the embodiments or variants of the present invention.

Figure 21:
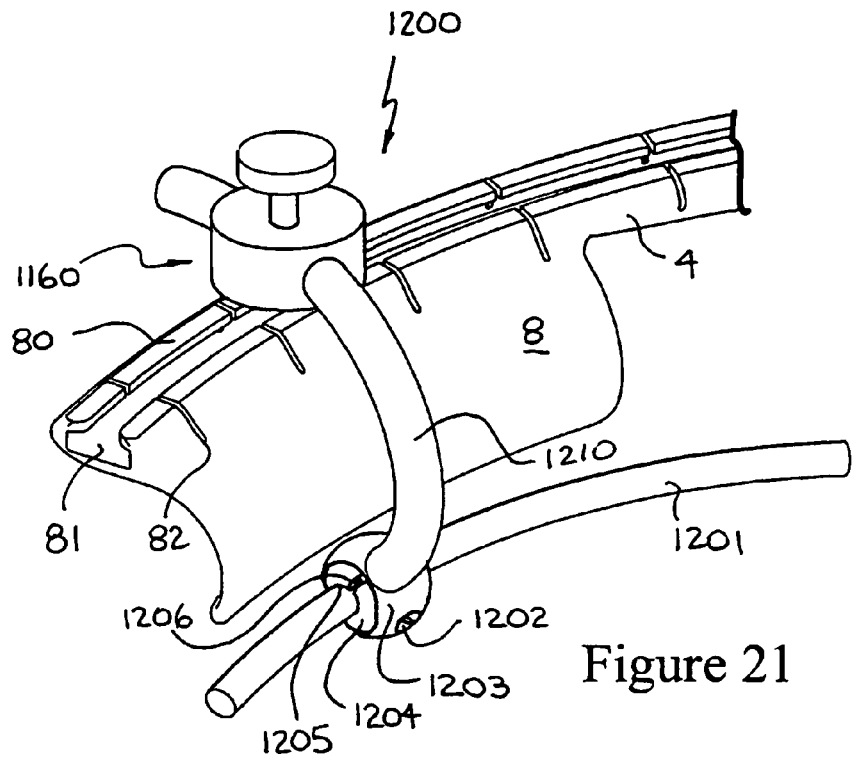
FIG. 21 is a perspective view illustrating a variant mechanical joint between deflection member and connection member in the nature of a pivoting joint, according to the present invention.

FIG. 21 illustrates a surgical deflector tool 1200 with a variant mechanical joint between deflection member 1201 and connection member 1210. Elongate deflection member 1201 is rod-like in cross-section and preferably arcuate in shape. Connection member 1210 is configured with a socket 1203 at its distal free end. Said socket 1203 retains a split sphere 1204 therein. Said sphere 1204 is configured with a through bore 1205 that is split lengthwise by slot 1206 that also extends radially outward to outer surface of said sphere 1204. Deflection member 1201 is inserted in bore 1205 and is free to slide within said bore. Once engaged with sphere 1204, said deflection member 1201 is capable of pivoting relative to connection member 1210 within the spherical joint defined by socket 1203 and sphere 1204. The position and orientation of deflection member 1201 relative to connection member 1210 may be locked or fixed by tightening a securing means in nature of screw 1202. As such, this variant defines a deflection member 1201 that is slidingly and pivotingly engaged with a connection member 1210.

Figure 22:
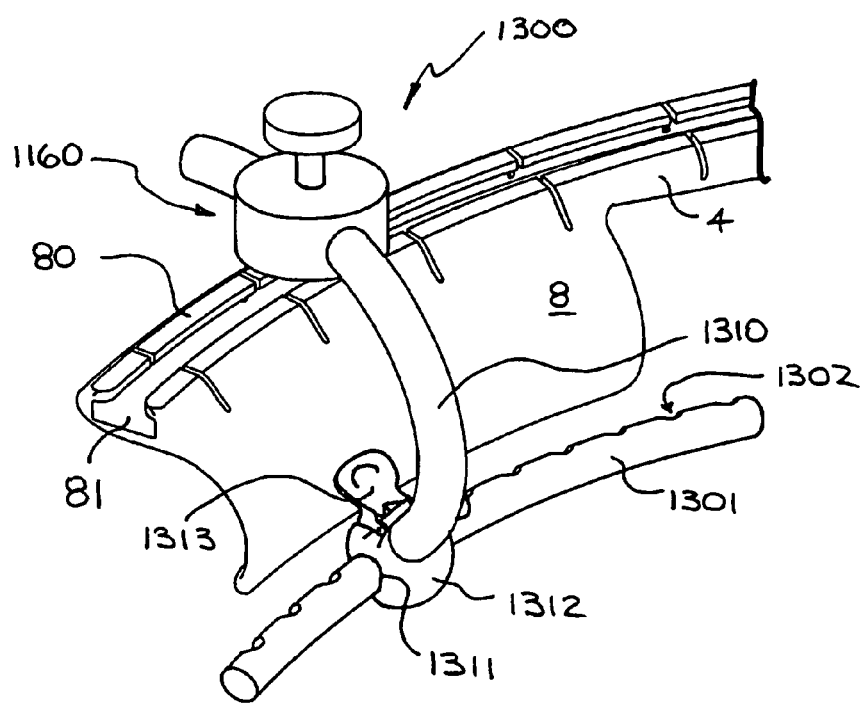
FIG. 22 is a perspective view illustrating a variant mechanical joint between deflection member and connection member in the nature of a sliding joint, according to the present invention.

FIG. 22 illustrates a surgical deflector tool 1300 with a variant mechanical joint between deflection member 1301 and connection member 1310. Elongate deflection member 1301 is rod-like in cross-section and preferably arcuate in shape and has a plurality of depressions or grooves 1302 disposed along its length. Connection member 1310 is configured with a fitting 1312 at its distal free end. Said fitting 1312 is configured with a through bore 1311. Fitting 1312 is provided with a slot or opening (not shown) that communicates with said through bore 1311. A detent lever 1313 is pivotingly engaged with fitting 1312. Said lever is configured with a protrusion or latch (not shown) which extends within said slot or opening in fitting 1312 and engages with a groove 1302 contained along the portion of deflection member 1301 engaged within bore 1311. Deflection member 1301 is capable of translating freely through fitting 1312 when lever 1313 is depressed by the surgeon, thereby disengaging said latch from groove 1302. As such, deflection member 1302 may be repositioned relative to connection member 1310. The position of deflection member 1301 relative to connection member 1310 may be locked or fixed by again releasing lever 1313 so that said latch engages another groove 1302. This variant defines a deflection member 1301 that is slidingly engaged with a connection member 1310.

Figure 23:
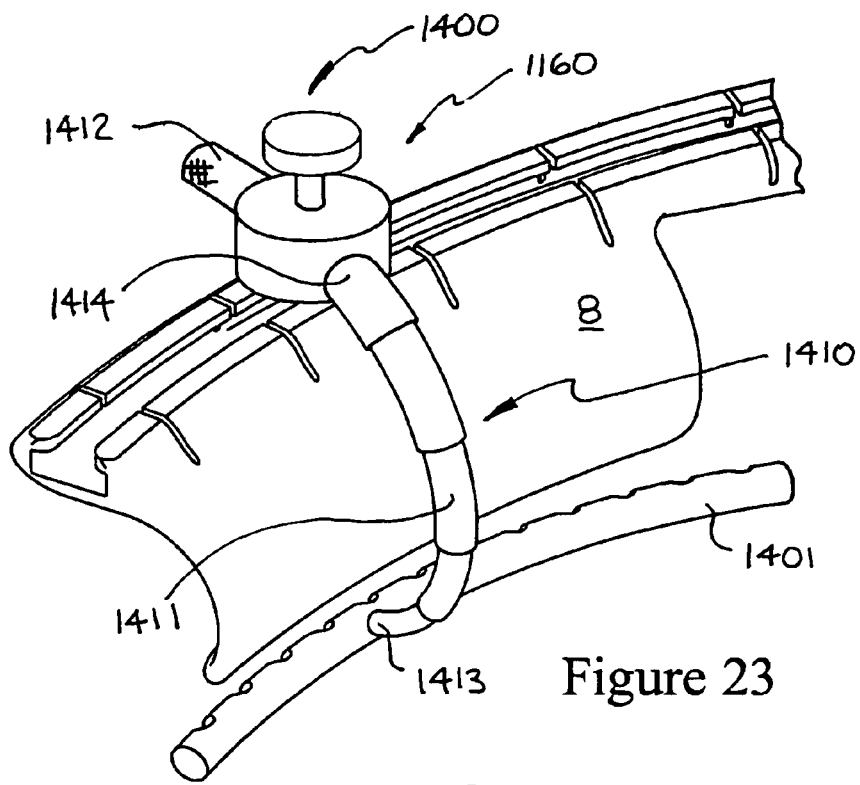
FIG. 23 is a perspective view illustrating a variant connection member in the nature of a collapsible and extendable telescopic arm, according to the present invention.

FIG. 23 illustrates a surgical deflector tool 1400 with a variant connection member in the nature of a collapsible and extendable telescopic arm 1410. Telescopic arm 1410 may be deployed in a substantially continuous range of variable connection arm lengths between its deflecting end 1413 and securing end 1414. Telescopic arm 1410 is comprised of a plurality of progressively smaller diameter tubular segments 1411 each capable of being retracted within the lumen of the adjacent larger diameter segment. Tubular segments 1411 are preferably arcuate in shape along their defining longitudinal axes. In its non-deployed configuration, telescopic arm 1410 is collapsed in length with deflecting end 1413 in close proximity to securing end 1414. The surgeon deploys deflector tool 1400 by extending telescopic arm 1410 in length until the deflection member 1401 is placed in contact with at least one tissue retraction means and the requisite deflection of said tissue retraction means is achieved at which point the telescopic arm is fixed in position. The tubular segments 1411 may be designed with sufficient sliding friction between adjacent segments such that said friction is sufficient to maintain telescopic arm in desired position to maintain desired deflection of tissue retraction means. Alternatively, a position-fixating knob 1412 may be disposed at the proximal end of telescopic arm 1410 to secure desired configuration of telescopic arm 1410. The concept of a telescopic arm may also be applied to deflection member 1401 so that a variable length deflection member may be deployed within the surgical workspace to best suit the patient anatomy or space available within the retracted chest cavity.

Figure 24:
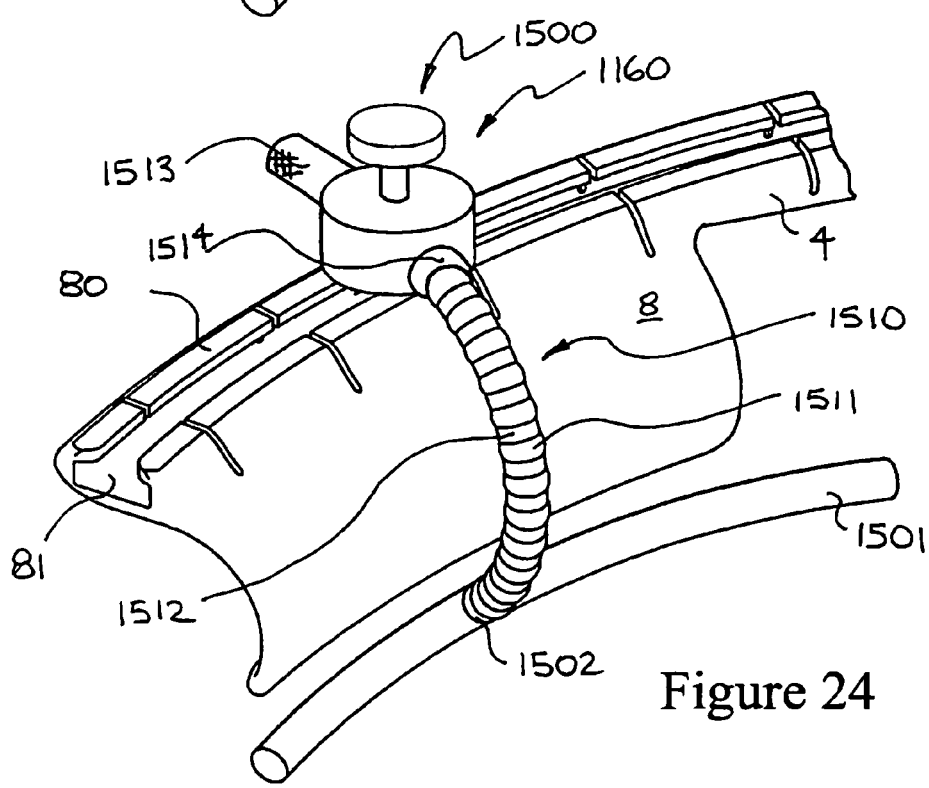
FIG. 24 is a perspective view illustrating a variant connection member in the nature of a flexible, lockable arm, according to the present invention.

FIG. 24 illustrates a surgical deflector tool 1500 with a variant connection member in the nature of a flexible, lockable arm 1510 having a plurality of interconnecting links 1511, 1512 which allow the positioning and orientation of deflection member 1501 in every direction within the surgical workspace until the desired configuration is achieved at which point the flexible arm 1510 may be locked into a fixed configuration by tightening a fixation knob 1513 attached to a cable (not shown) running axially through the interconnecting links 1511, 1512. Interconnecting link 1511 is comprised of a ball portion or sphere joint which fits conformingly within a receiving portion or cylindrical tube of interconnecting link 1512. When a tension is exerted on said cable, flexible arm 1510 is locked in a rigid configuration. Alternatively, other tensioning means are also possible. For instance, an inflatable internal balloon that expands against the interior of said interconnecting links rendering the individual links immobile, and thereby locking the entire arm 1510 into a fixed configuration, or other like means for securing interconnecting links of a flexible arm.

The proximate end 1514 of arm 1510 is attached to sternum retractor 5 through securing mechanism 1160. When fixation knob 1513 is not actuated, flexible arm 1510 is deformable between points 1514 and 1502. As such, arm 1510 may assume not only an arcuate shape (as illustrated in FIG. 24), but any other shape such as a spline, S-shape, or other variant shape which is most suited for the surgical field in which deflector tool 1500 will be deployed. The concept of a flexible, lockable arm may also be applied to deflection member 1501 so that a deformable deflection member may be deployed within the surgical workspace to best suit the patient anatomy or space available within the retracted chest cavity.

Figure 25:
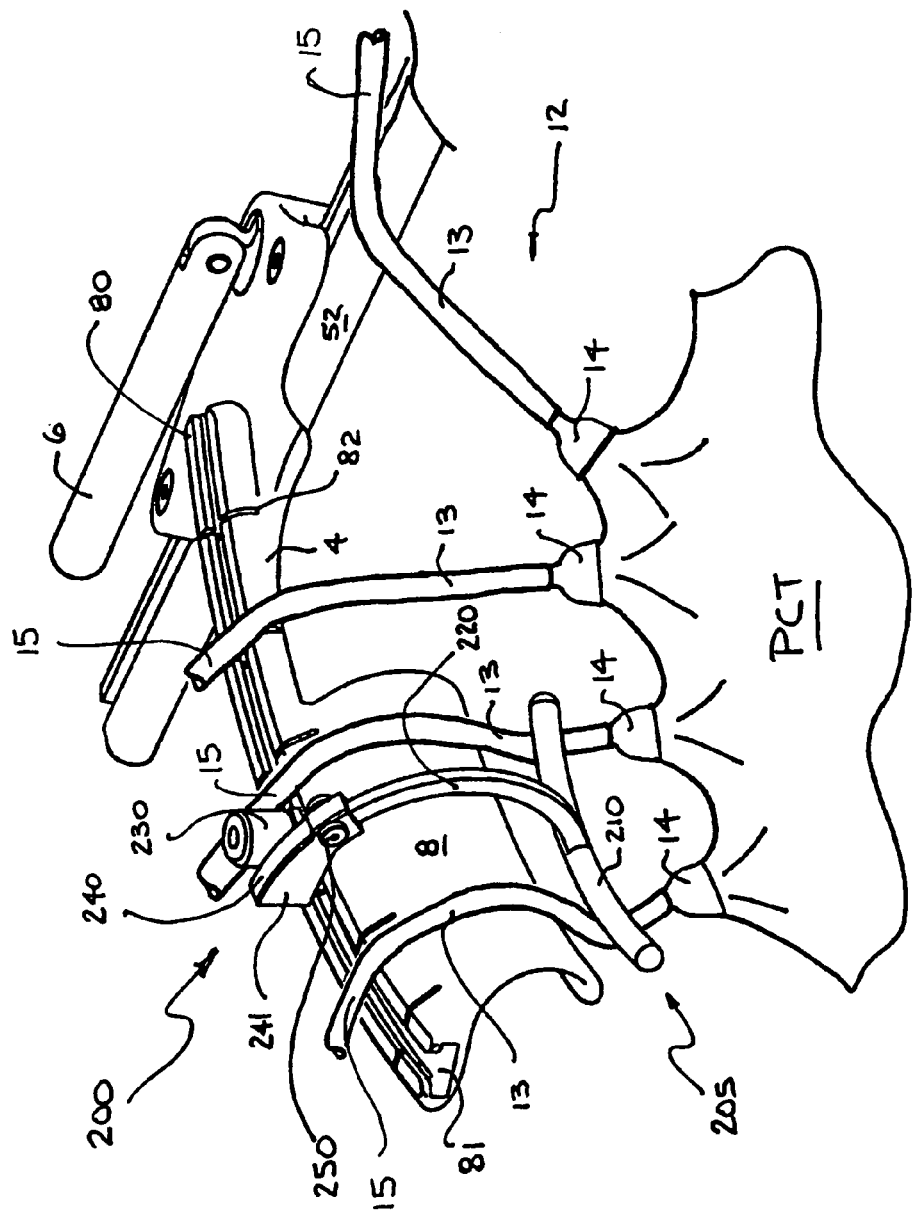
FIG. 25 is a perspective view illustrating a surgical deflector tool and a surgical apparatus with which the said surgical deflector tool may be used, according to a thirteenth embodiment of the present invention.

FIG. 25 illustrates a surgical deflector tool 200 from the second embodiment, engaged with a plurality of tissue retraction means in the nature of suction device 12. Suction device 12 is comprised of a suction port 14 (preferably deformable) disposed at its distal free end, and a substantially flexible hollow conduit 13 providing a negative pressure suction force from a distal vacuum source to said port 14. In use, said suction device is engaged at its proximal end 15 with a portion of passage 81, 71, or 51 of sternum retractor 5, and simultaneously engaged at its distal end with pericardium tissue PCT through said suction port 14. Surgical deflector tool 200, when deployed, serves to deflect at least a portion of said suction device, more specifically its conduit 13, in a similar manner as already described in relation to surgical suture tissue retraction means. Instead of surgical deflector 200, other embodiments of a surgical deflector tool already described may also be used to cooperate with suction device 12.

In the embodiments of the present invention described herein, it is intended to produce the bulk of the surgical apparatus from reusable components, whose assembly may be at least partially dismantled, if necessary, for ease of sterilization. All components are manufactured in either surgical grade stainless steel, titanium, aluminum or any other reusable sterilizable material suitable for surgical use. Components that may be produced from polymeric materials are either reusable through specific sterilization procedures tailored to these component materials, or must be replaced after every use or after a predetermined number of uses if the polymeric material properties are not suitable for sterilization or degrade after repeated sterilization cycles. However, any number of the said reusable components may also be produced from disposable surgical grade plastics, if the case for disposable components is warranted and if the engineering and functional intent is maintained when the said component is produced from plastic.

The above description of the embodiments of the present invention should not be interpreted in any limiting manner since variations and refinements are possible without departing from the spirit of the invention.

What is claimed is:

1. A suture deflector for retracting a body tissue of a patient by deflecting a surgical suture attached to said body tissue, said body tissue being located within a body cavity of said patient, said body cavity being located generally below the skin surface of said patient, said body tissue being accessed during surgery through a surgical window in said skin surface, said surgical window being created by a skin retractor, said body tissue being retracted in a first retracted position generally along a first retraction direction when said surgical suture is tensioned between said body tissue and said skin retractor without being deflected by said suture deflector, said suture deflector comprising:

a securing mechanism for attachment to said skin retractor;

a deflection member extending from said securing mechanism, said deflection member defining a suture contacting section for contacting said surgical suture intermediate said body tissue and said skin retractor and imparting a deflecting force on said surgical suture, said suture contacting section being configured so as to prevent the severing of said surgical suture upon said deflecting force being applied thereon, said deflection member being configured and sized so as to minimize obstruction of said surgical window when said surgical suture is deflected by said deflection member;

said suture deflector being movable between a non-deflecting configuration and a deflecting configuration, wherein in said non-deflecting configuration said suture contacting section contacts said surgical suture while said body tissue remains retracted in said first retracted position, and, in said deflecting configuration, said suture contacting section imparts said deflecting force on said surgical suture causing said body tissue to be retracted towards a second retracted position generally along a second retraction direction.

2. A suture deflector as recited in claim 1, wherein said deflection member is configured so that said suture contacting section is located substantially underneath said skin retractor when said suture deflector is in said deflecting configuration.

3. A suture deflector as recited in claim 1, wherein said securing mechanism is movable between a loosened condition and a locked condition;

in said loosened condition, said securing mechanism is movable relative to said skin retractor while said securing mechanism is engaged thereto, and said deflection member is movable relative to said securing mechanism; and in said locked condition, said securing mechanism is fixed relative to said skin retractor, said deflection member is fixed relative to said securing mechanism, and said body tissue is retracted in said second retracted position by said suture contacting section applying said deflecting force to said surgical suture.

4. A suture deflector as recited in claim 1, wherein said suture contacting section has a friction enhancing texture on at least a portion thereof to improve engagement with said surgical suture.

5. A suture deflector as recited in claim 1, wherein said suture contacting section is provided with a slot on at least a portion thereof, said slot configured to laterally restrain said surgical suture as said body tissue is being retracted between said first and second retracted positions.

6. A suture deflector as recited in claim 1, wherein said deflection member includes a connecting section extending between said securing mechanism and said suture contacting section, said connecting section being configured and sized so as to be in a substantially adjacent and parallel relationship with said skin retractor when said suture deflector is in said deflecting configuration.

7. A suture deflector as recited in claim 6, wherein said connecting section has a substantially convex configuration relative to said surgical window.

8. A suture deflector as recited in claim 6, wherein at least one of said suture contacting section or said connecting section is substantially elongate and generally arcuate in shape.

9. A suture deflector as recited in claim 8, wherein said suture contacting section is attached to said connecting section to form a substantial L-shaped arrangement.

10. A suture deflector as recited in claim 8, wherein said suture contacting section is attached to said connecting section to form a substantial T-shaped arrangement.

11. A suture deflector as recited in claim 8, wherein said suture contacting section has a friction enhancing texture on at least a portion thereof to improve engagement with said surgical suture.

12. A suture deflector as recited in claim 8, wherein said suture contacting section is provided with a slot on at least a portion thereof, said slot configured to laterally restrain said surgical suture as said body tissue is being retracted between said first and second retracted positions.

13. A suture deflector as recited in claim 6, wherein said connecting section is movable relative to said securing mechanism, said relative movement causing said suture contacting section to impart said deflecting force on said surgical suture and causing said body tissue to be retracted towards said second retracted position.

14. A suture deflector as recited in claim 13 further comprising an adjustment mechanism, wherein said adjustment mechanism selectively fixing the spatial relationship of said connecting section relative to said securing mechanism to provide said deflecting configuration.

15. A suture deflector as recited in claim 14 further comprising an actuation member, said actuation member operatively coupled to said connecting section and said adjustment mechanism, whereby when said actuation member is actuated said connecting section is movable relative to said securing mechanism.

16. A suture deflector as recited in claim 14, wherein said adjustment mechanism being configured to allow movement of said connecting section relative thereto when a force is applied in a first movement direction, and restrict movement of said connecting section relative thereto when a force is applied in a generally opposed direction to said first movement direction.

17. A suture deflector as recited in claim 6, wherein said connecting section is a telescopic arm, said telescopic arm movable between a collapsed configuration and an extended configuration providing a substantially continuous range of variable connecting section lengths between said securing mechanism and said suture contacting section.

18. A suture deflector as recited in claim 6, wherein said connecting section is a substantially flexible lockable arm providing movement of said suture contacting section relative to said securing mechanism.

19. A suture deflector as recited in claim 6, wherein said suture contacting section is operatively coupled to said connecting section through a mechanical joint, said mechanical joint allowing relative movement between said suture contacting section and said connecting section, said relative movement causing said suture contacting section to impart said deflecting force on said surgical suture and causing said body tissue to be retracted towards said second retracted position.

20. A suture deflector as recited in claim 19, wherein said suture contacting section is rotatably connected to said connecting section through said mechanical joint.

21. A suture deflector as recited in claim 19, wherein said suture contacting section is slidingly connected to said connecting section through said mechanical joint.

22. A suture deflector as recited in claim 19, wherein said suture contacting section is pivotally connected to said connecting section through said mechanical joint.

23. A suture deflector as recited in claim 19, wherein said mechanical joint includes an adjustment mechanism, said adjustment mechanism being operatively coupled to said suture contacting section, wherein said adjustment mechanism selectively fixing the spatial relationship of said suture contacting section relative to said connecting section to provide said deflecting configuration.

24. A suture deflector as recited in claim 19 further comprising an actuation member, said actuation member operatively coupled to said suture contacting section and said connecting section, whereby when said actuation member is actuated said suture contacting section is movable relative to said connecting section.

* * * * *